United States Patent

Takekawa et al.

[11] Patent Number: 5,175,086
[45] Date of Patent: * Dec. 29, 1992

[54] METHOD FOR EFFECTING HETEROGENEOUS IMMUNOLOGICAL ANALYSIS

[75] Inventors: Hiroshi Takekawa; Takashi Yamada, both of Sagamihara, Japan

[73] Assignee: Olympus Optical Co., Ltd., Tokyo, Japan

[ * ] Notice: The portion of the term of this patent subsequent to Jun. 6, 2006 has been disclaimed.

[21] Appl. No.: 119,278

[22] Filed: Nov. 9, 1987

Related U.S. Application Data

[63] Continuation of Ser. No. 573,318, Jan. 24, 1984, abandoned.

[30] Foreign Application Priority Data

| Jan. 24, 1983 | [JP] | Japan | 58-9598 |
| Jan. 24, 1983 | [JP] | Japan | 58-9599 |
| Feb. 14, 1983 | [JP] | Japan | 58-21555 |
| Apr. 18, 1983 | [JP] | Japan | 58-68161 |

[51] Int. Cl.$^5$ .................. G01N 33/535; C12M 1/40
[52] U.S. Cl. .................. 435/7.92; 435/7.93; 435/7.94; 435/288; 435/291; 435/808; 436/518; 436/45; 436/47; 436/48; 422/63; 422/64
[58] Field of Search .................. 435/7, 288, 291, 292, 435/293, 296, 299, 300, 301, 313, 315, 7.1, 7.9, 7.92, 7.93, 7.94, 7.95, 188, 808; 436/518, 527, 531, 808, 809, 535, 43, 45, 47, 48, 49; 422/64, 65, 67, 68, 73, 100, 63, 102

[56] References Cited

U.S. PATENT DOCUMENTS

| 2,653,083 | 9/1953 | Wanzer et al. | 422/64 |
| 2,788,812 | 1/1974 | Dupre | 436/808 X |
| 3,489,525 | 1/1970 | Natelson | 422/64 |
| 3,592,605 | 7/1971 | Noma et al. | 422/64 |
| 3,912,452 | 10/1975 | Sodickson et al. | 422/64 X |
| 3,917,455 | 11/1975 | Bak et al. | 422/64 |
| 3,951,605 | 4/1976 | Natelson | 436/808 X |
| 4,101,284 | 7/1978 | Difiglio et al. | 422/100 |
| 4,158,545 | 6/1979 | Yamashita et al. | 422/67 X |
| 4,200,607 | 4/1980 | Suzuki | 422/64 |
| 4,315,891 | 2/1982 | Sakurada | 422/64 |
| 4,363,781 | 12/1982 | Akamatsu et al. | 422/67 X |
| 4,383,041 | 5/1983 | Kutsusawa et al. | 436/808 X |
| 4,454,095 | 6/1984 | Holt | 422/64 |
| 4,459,265 | 7/1984 | Berglund | 436/47 |
| 4,512,852 | 4/1985 | Tsuboshima et al. | 422/64 X |
| 4,528,159 | 7/1985 | Liston | 422/67 X |
| 4,536,369 | 8/1985 | Sakurada et al. | 422/64 X |
| 4,540,549 | 9/1985 | Manabe | 422/64 |
| 4,567,021 | 1/1986 | Sakagami | 422/64 X |
| 4,837,159 | 6/1989 | Yamada | 422/67 |

FOREIGN PATENT DOCUMENTS

| 3210886 | 10/1982 | Fed. Rep. of Germany | 422/64 |
| 56-147067 | 11/1981 | Japan . | |
| 57-74662 | 5/1982 | Japan . | |

OTHER PUBLICATIONS

Maggio (editor), Enzyme-Immunoassay, CRC Press, Boca Raton, Fla., (1980), pp. 168-173 and 178.
Ruitenberg et al., Scandinavian Journal of Immunology, Supplement No. 7, vol. 8, (1978), pp. 63-72.

Primary Examiner—Robert J. Warden
Assistant Examiner—William H. Beisner
Attorney, Agent, or Firm—Stevens, Davis, Miller & Mosher

[57] ABSTRACT

Method for generating an automatic chemical analyzer for measuring given substances in samples in accordance with an enzyme-immunoassay including a turntable rotated intermittently at a given pitch and holding a number of reaction tubes arranged equidistantly along a periphery of the turntable to define a circular reaction line; a carrier supply device for supplying carriers into reaction vessels one by one at a given position in the reaction line, the carrier having given antibody or antigen fixed thereto; a sample delivery device for pouring given amounts of samples into reaction vessels at a given position in the reaction line; a washing device for washing reaction vessels and carriers contained therein to effect B-F separation; a color reagent delivery device for pouring given amounts of a color reagent into reaction vessels to form test liquids; a colorimeter for photometering the test liquids; and a carrier discharge device for removing carriers out of reaction vessels. For respective samples, a reaction vessel is passed through the washing device by a plurality of times to perform a plurality of washing operations including the B-F separation.

27 Claims, 30 Drawing Sheets

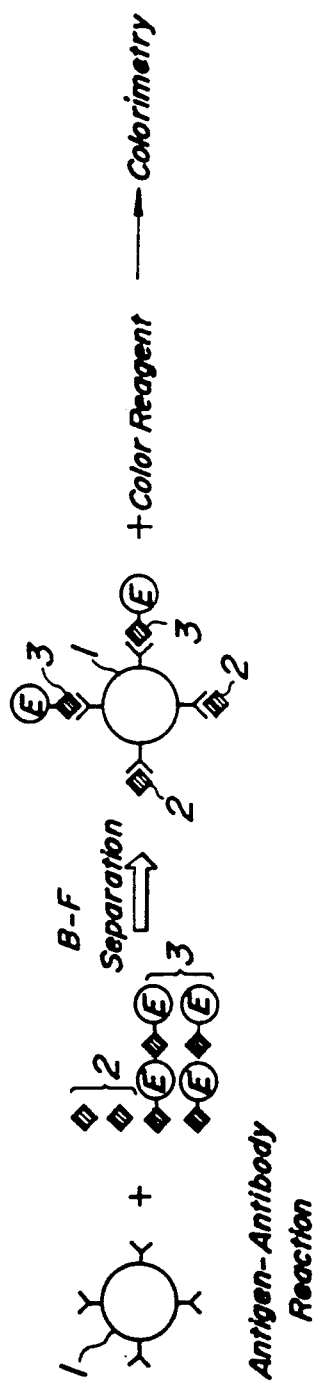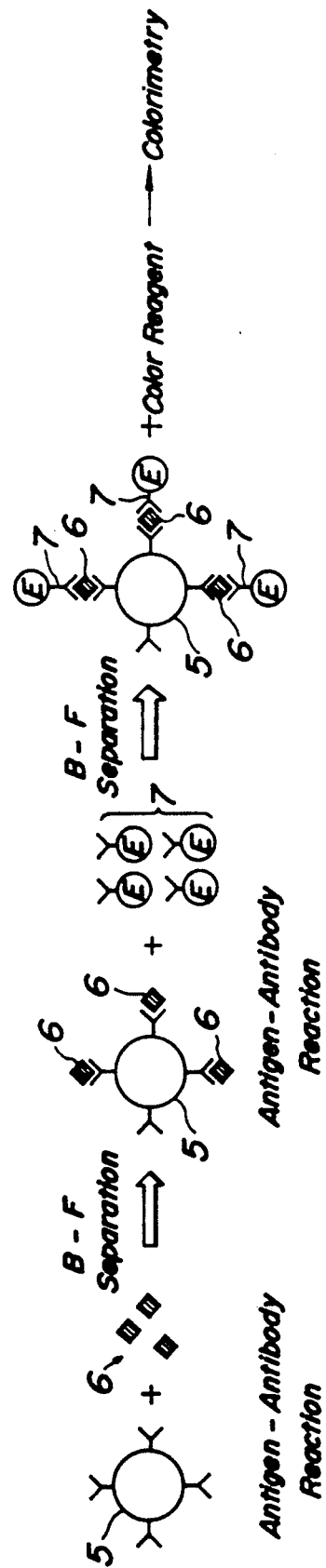

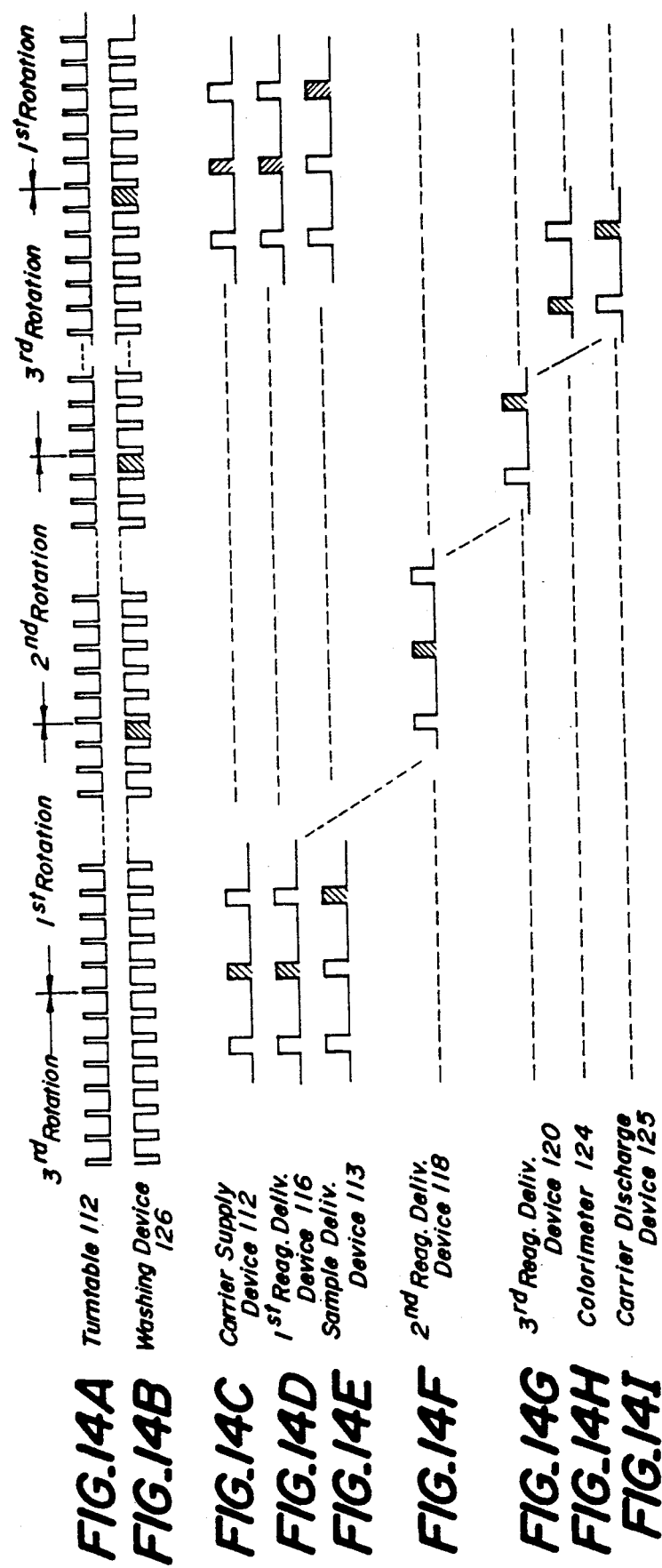

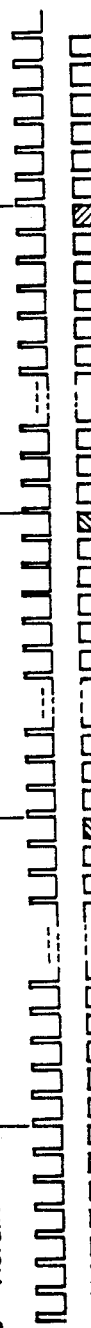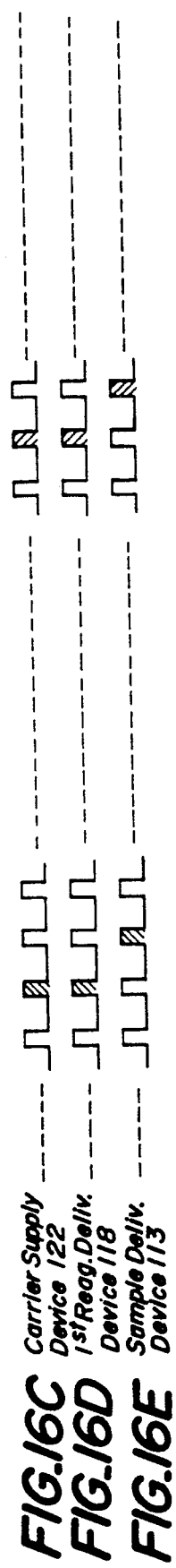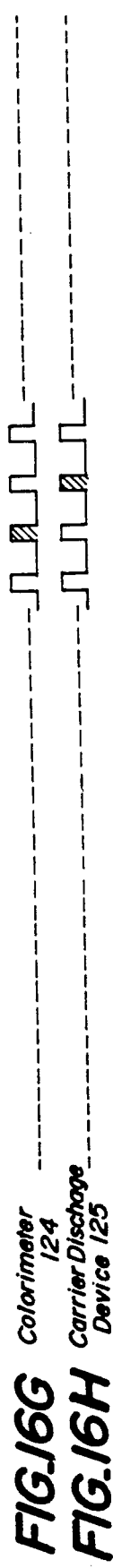
FIG.16A Turntable 112
FIG.16B Washing Device 126
FIG.16C Carrier Supply Device 122
FIG.16D 1st Reag.Deliv. Device 118
FIG.16E Sample Deliv. Device 113
FIG.16F 2nd Reag.Deliv. Device 120
FIG.16G Colorimeter 124
FIG.16H Carrier Discharge Device 125

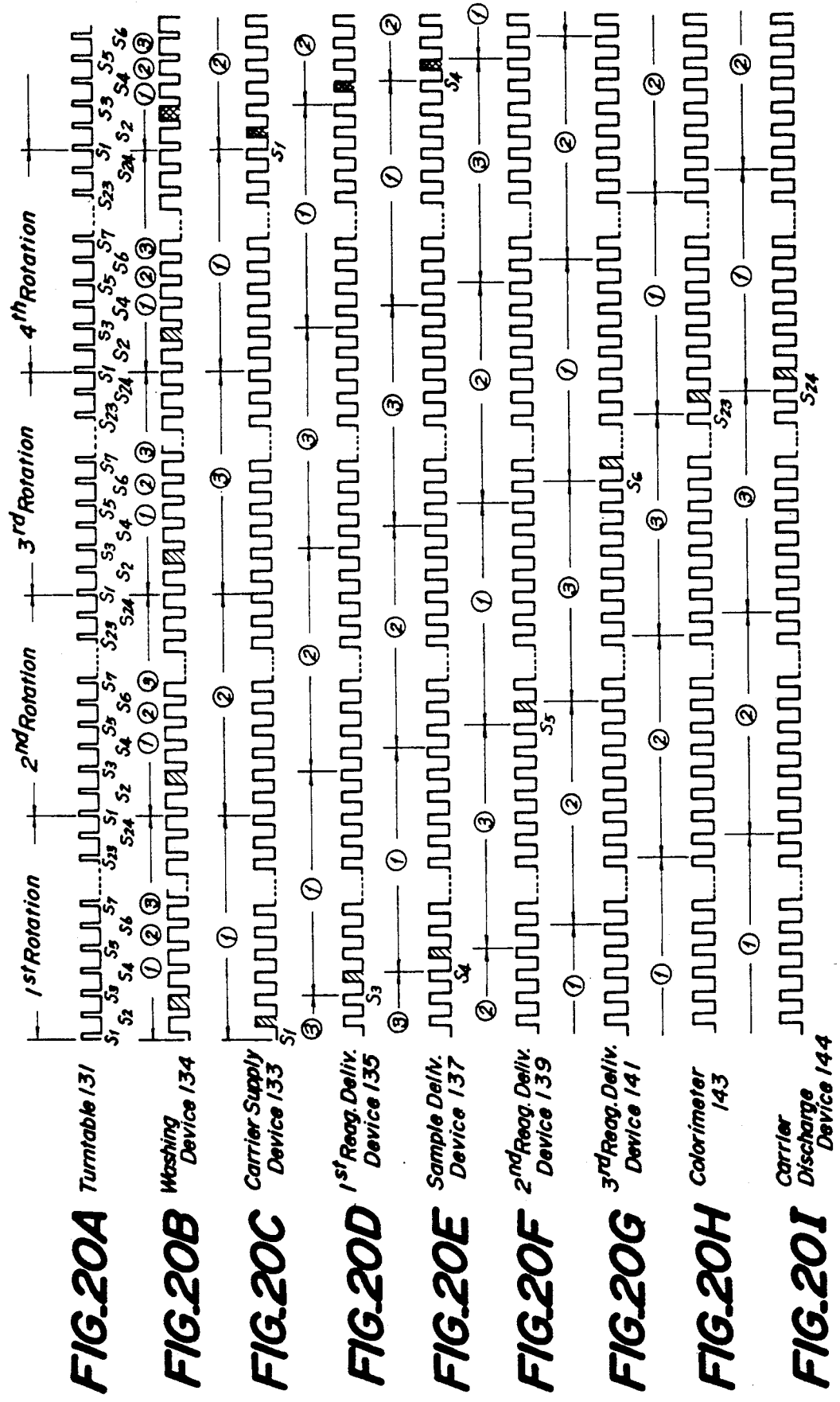

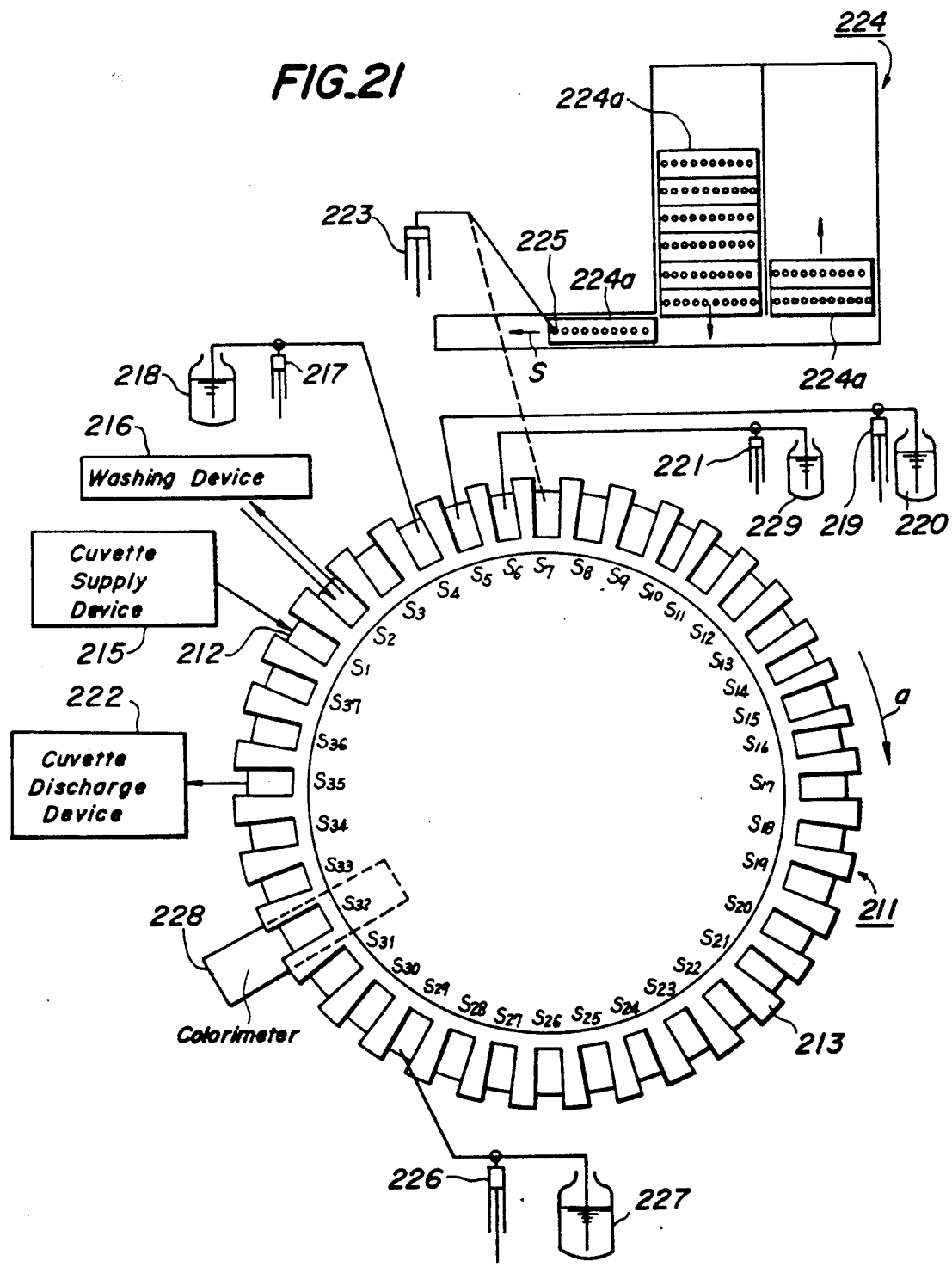

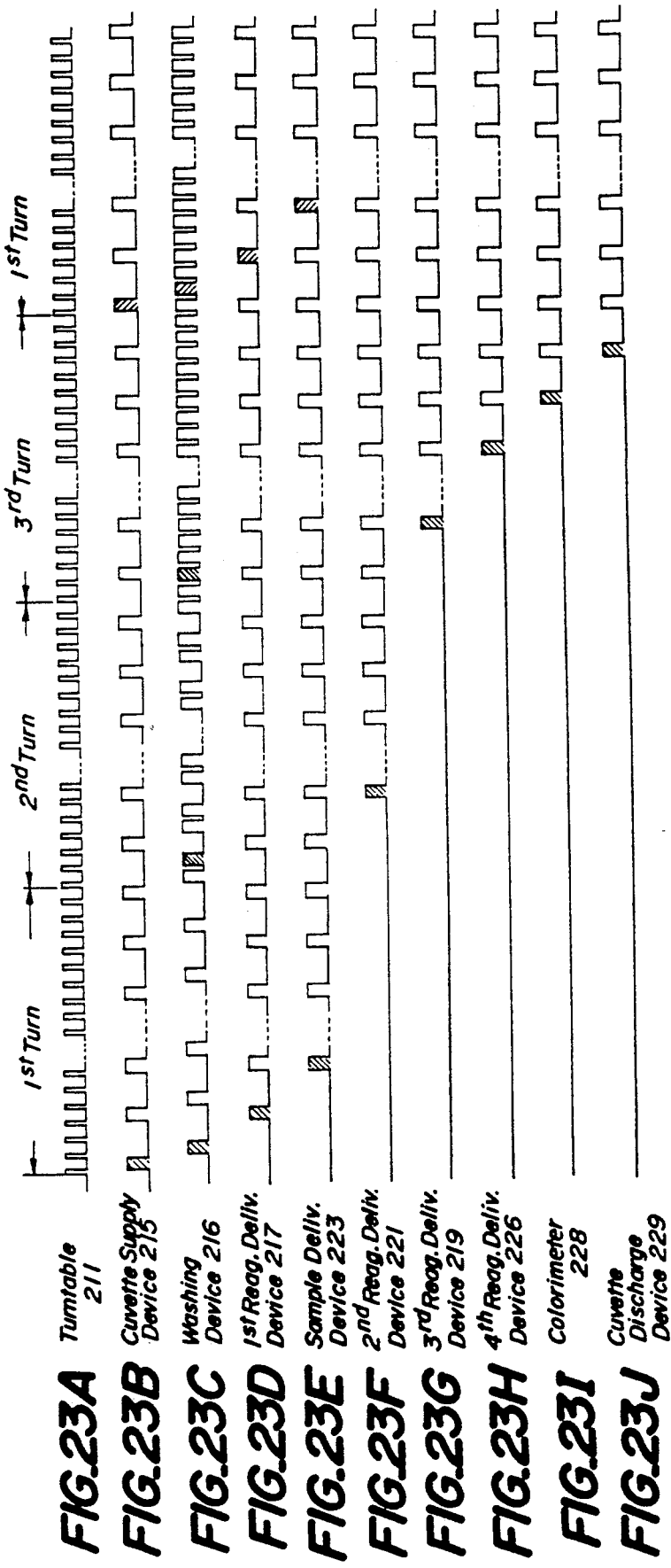

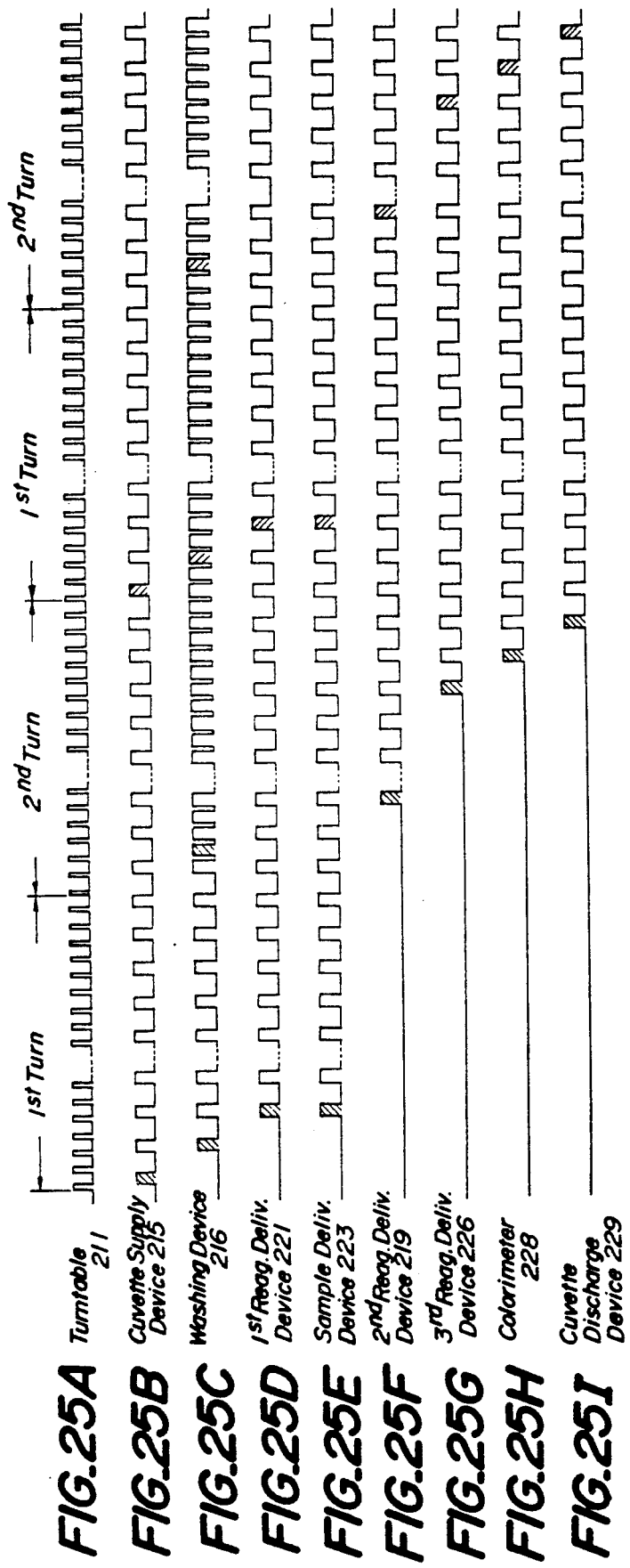

METHOD FOR EFFECTING HETEROGENEOUS IMMUNOLOGICAL ANALYSIS

This application is a CONTINUATION of application Ser. No. 573,318, filed Jan. 24, 1984, now abandoned.

BACKGROUND OF THE INVENTION

The present invention relates generally to immunological analysis and more particularly to a method of analyzing automatically given substances in samples due to an immunological reaction of antigen and antibody.

At present, due to progress in medical treatment, very small amounts of biological substances in samples can be analyzed and this contributes to early diagnosis for various diseases. For instance, malignant tumors such as α-fetoprotein and carcinoembryonic antigen, diseases in abnormal secretory of hormone such as insulin and thyroxine, and immunological diseases such as immunoglobulin can be diagnosed in early stages and further the monitoring after treatments for these diseases can be carried out reliably. Moreover, the measurement of incomplete antigens, i.e. low molecular hapten of medical substances contributes to development of a plan of medication.

Many biological substances are analyzed in an immunological manner by utilizing the antigen-antibody reaction and various methods for effecting the immunological analysis have been developed. For instance, existence or non-existence of agglinated clots of antigen-antibody compound formed by the antigen-antibody reaction is detected by agglutination method, sedimentry method, nephelometry method, etc. to analyze desired biological substances. However, in the known methods, since the sensitivity is low, a large amount of antigen-antibody compound is required and only qualitative analyses or quasi-quantitative analyses can be performed. In order to avoid such a drawback, there have been further proposed the following methods. In one of the known methods, antigen or antibody is bound with carbon or synthetic resin fine particles which are then subjected to the antigen-antibody reaction with the biological substances to be analyzed and the substances are detected by means of the agglutination method or nephelometry method. In another known method, antigen-antibody compounds are detected at a high sensitivity by using antigen or antibody marked with labeling material such as radioisotope, fluorescent material, luminescent material and enzyme. However, since the former method is inferior to the latter method in the sensitivity, recently the latter method using the high sensitivity labeling substance has been predominantly adopted.

The analytic methods using the markers are classified into radio-immuno-assay using radioisotope tracers, fluorescent-immuno-assay using fluorescent labeling material, and enzyme-immuno-assay using enzyme markers. Among these methods, the enzyme-immuno-assay has been particularly developed owing to the reason that it does not require special installation and measuring technique and can be performed easily by using commonly developed colorimeters. The enzyme-immuno-assay is further classified into homogeneous enzyme-immuno-assay and heterogeneous enzyme-immuno-assay. In the homogeneous analysis, a variation in activity of labeling enzyme due to existence or non-existence of the immunological reaction is directly measured to detect substances to be analyzed. In the heterogeneous analysis, use is made of insoluble carriers such as glass beads or synthetic resin particles on which antigen or antibody has been fixed, enzyme-labeled antigen or antibody bound with the antibody or antigen fixed on the carriers and free enzyme-labeled antigen or antibody not bound with the antibody or antigen on the carriers are separated from each other by washing treatment, and then an activity of labeling enzyme is detected to measure a quantity of substances to be analyzed. Hereinbelow, the process for separating the bound antigen or antibody and the free antigen or antibody from each other is termed as B-F or bound-free separation for the sake of simplicity. Although the homogeneous analysis can be performed by simple processes, it can analyze only the low molecular hapten such as medical substances, but cannot analyze high molecular biological substances. Contrary to this, in the heterogeneous analysis, although the washing process is required for effecting the B-F separation, it can be applied to any kinds of low and high molecular substances. Therefore, recently the heterogeneous enzyme-immuno-assay has been generally adopted.

In the heterogeneous enzyme-immuno-assay, there have been developed competitive method and sandwich method. Now these methods will be explained with reference to the drawings.

FIG. 1 illustrates successive steps of the competitive method. Given antigen or antibody which reacts with antibody or antigen substances 2 of a sample has been previously fixed to an outer surface of a insoluble carrier 1. At first, the antigen-antibody reaction is carried out between the antigen or antibody fixed onto the carrier 1 and the antibody or antigen 2 in the sample as well as a labeled reagent 3 which has been prepared by labeling substances same as the substances 2 to be analyzed with enzyme marker. Then, a washing process is carried out to effect the B-F separation between the substance 2 and labeled reagent 3 bound with the carrier 1 due to the antigen-antibody reaction and free substances 2 and reagent 3 which are not bound with the carrier 1. Next, a color reagent which selectively reacts with the labeling enzyme is added and a reaction liquid is colorimetered to detect the enzyme activity of the labeling enzyme.

FIG. 2 shows successive steps of the sandwich method in which use is made of an insoluble carrier 5 having fixed thereto antibody or antigen which is reactive with antigen or antibody substances in a sample to be tested. At first, the carrier 5 and the sample 6 are mixed to effect the antigen-antibody reaction between the substances 6 in the sample and the antibody or antigen fixed to the carrier 5. Then, the B-F separation is carried out by means of the washing step. Next, a labeled reagent 7 is added to effect the antigen-antibody reaction. The labeled reagent is prepared by marking with enzyme substance selectively reacting with the substance 6 to be analyzed. Then, after the B-F separation is effected again, a color reagent reacting with the labeling enzyme in the labeled reagent 7 is added and a test liquid thus obtained is colorimetered to detect the activity of the labeling enzyme.

As explained above, in the heterogeneous immuno-assay the B-F separation has to be carried out once in the competitive method and twice in the sandwich method during the analysis for respective sample and further if a reaction vessel for effecting the antigen-antibody reaction is used repeatedly, there must be further provided a step for washing the reaction vessel after the end of analysis for a sample, but before the start of analysis for another sample. In case of automating the enzyme-immuno-assay requiring at least two washing steps including the B-F separation, separate washing devices may be provided at different positions. However, then an automatic analyzer is liable to be large in size, complex in construction and expensive in cost. This disadvantage will also appear in automatic analyzer effecting radio-immuno-assay and fluorescent-immuno-assay.

In a Japanese Patent Application Laid-open Publication No. 74,662/82 published on May 10, 1982, there is disclosed an automatic enzyme-immuno assay apparatus in which the B-F separation is effected by removing a carrier having antigen-antibody compound bound thereto from a reaction vessel to another reaction vessel. It is apparent such an analyzer becomes large in size and requires a special mechanism for transporting the carrier. Further, the efficiency of analysis is low and a number of samples could not be processed promptly. In a Japanese Patent Application Laid-open Publication No. 124,254/82 published on Aug. 3, 1982, there is described an automatic analyzer for effecting an immunological analysis in which the B-F separation is performed by rotating a rotor on which reaction vessels having carriers contained therein are arranged. In this analyzer, since the excess liquid is discharged in all directions due to the centrifugal force, the treatment of the discharged liquid becomes cumbersome. Further, since the reaction vessels containing the carriers are repeatedly used, a special treatment for releasing the antigen or antibody from the carriers must be effected between successive analyses.

SUMMARY OF THE INVENTION

The present invention has for its object to provide a method for effecting automatically an immunological analysis which can be carried out stably and effectively by a small, simple and inexpensive apparatus.

According to the invention, a method of automatically analyzing given substances in samples in an immunological manner comprises:

transporting a number of reaction vessels containing carriers onto which given antibody or antigen has been fixed or a number of reaction vessels having given antibody or antigen fixed onto at least a part of inner walls, along a reaction line;

delivering samples and labeled reagents into the reaction vessels to initiate antigen-antibody reaction;

effecting a B-F separation by separating antigen or antibody bound with the carriers or reaction vessels and free antigen or antibody from each other by means of washing;

measuring the given substances in the samples with the aid of labeling substances of the labeled reagent; and discharging the carriers or the reaction vessels out of the reaction line.

The present invention also relates to an automatic analyzer for carrying out the above method and has for its object to provide a novel and useful automatic analyzer which can be made simple in construction, small in size and inexpensive in cost.

According to the invention, an automatic analyzer for analyzing given substances in samples in an immunological manner comprises:

means for transporting a number of reaction vessels along a given reaction line;

means for supplying carriers into reaction vessels at a given position in the reaction line, said carriers having given antibody or antigen fixed thereto;

means for supplying given amounts of samples into the reaction vessels at a given position of the reaction line;

means for delivering given amounts of a labeled reagent into the reaction vessels at given positions in the reaction line;

means for washing the reaction vessels and carriers to effect a B-F separation for separating antigen or antibody bound with the carriers and free antigen or antibody;

means for measuring the given substances in the samples with the aid of labeling substances of the labeled reagent; and means for discharging the carrier from the reaction line.

The present invention further relates to a reaction vessel for use in the above method and has for its object to provide a novel reaction vessel for use in the immunological analysis.

According to the invention, a reaction vessel for use in a method of analyzing given substances in samples with the aid of given antibody or antigen fixed to solid substance and a labeled reagent having given antibody or antigen labeled with given substance, by supplying reaction vessels into a reaction line, delivering the samples and reagent into the reaction vessels, washing the reaction vessels to effect a B-F separation, measuring the given substances in the samples with the aid of the labeled reagent and discharging the reaction vessels from the reaction line, comprises:

a main body having an opening at its top; and a given antibody or antigen layer fixed onto at least a part of an inner wall of the main body.

BRIEF DESCRIPTION OF THE DRAWINGS

FIG. 1 is a schematic view showing successive steps of a known competitive method;

FIG. 2 is a schematic view illustrating successive steps of a known sandwich method;

FIGS. 14A to 14I are timing charts for explaining the operation of the automatic analyzer shown in FIG. 12;

FIGS. 16A to 16H are timing charts for explaining an operation of the automatic analyzer shown in FIG. 15;

FIGS. 20A to 20I are timing charts for explaining an operation of the automatic analyzer shown in FIG. 19;

FIG. 21 is a schematic view showing still another embodiment of the enzyme-immuno-assay automatic analyzer according to the invention;

FIGS. 23A to 23J are timing charts for explaining the operation of the automatic analyzer shown in FIG. 21;

FIGS. 25A to 25I are timing charts for explaining an operation of the automatic analyzer shown in FIG. 24;

DESCRIPTION OF THE PREFERRED EMBODIMENTS

Figure 3:
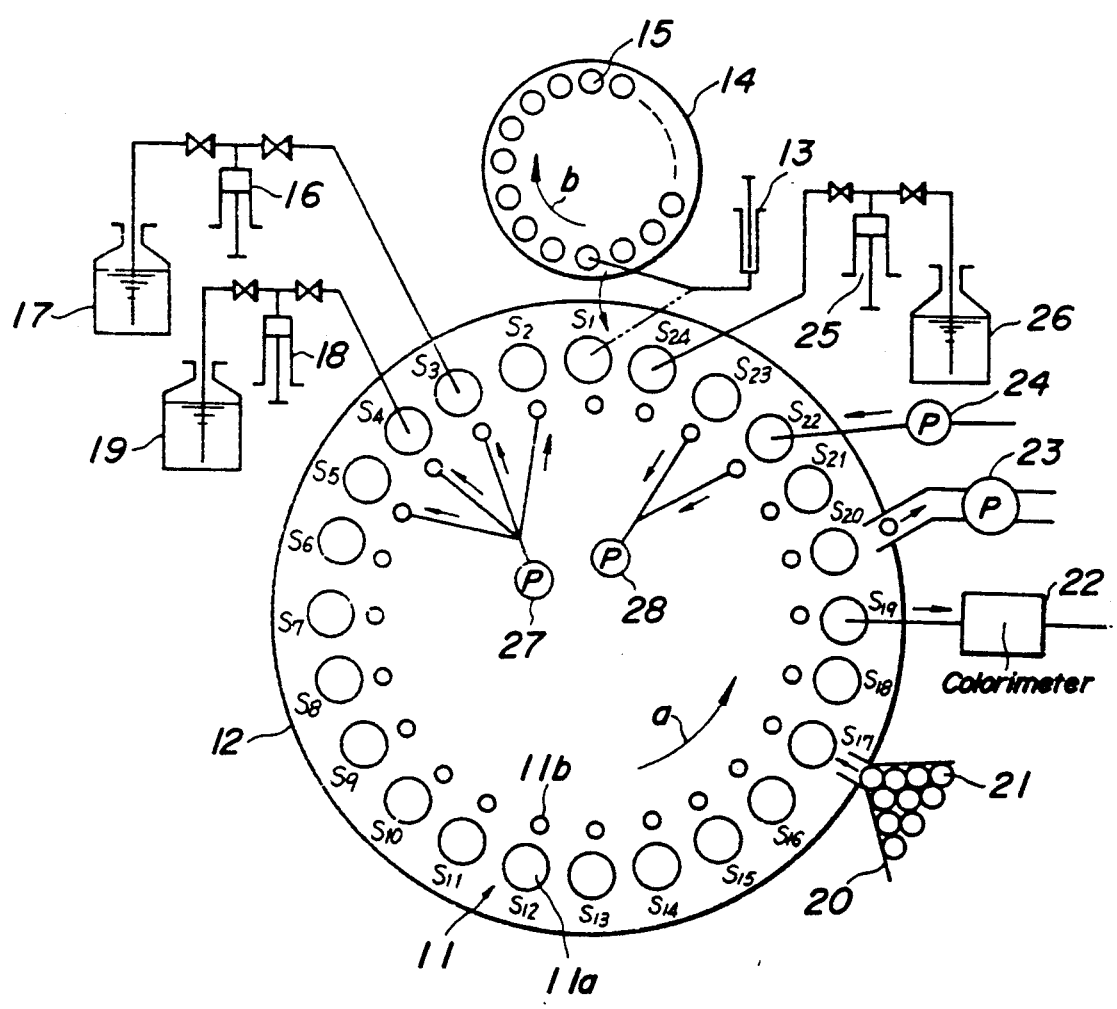
FIG. 3 is a schematic view depicting an embodiment of an enzyme-immuno-assay automatic analyzer according to the invention.

FIG. 3 is a schematic view showing an embodiment of the enzyme-immuno-assay automatic analyzer according to the invention which performs the sandwich method explained above with reference to FIG. 2. In the present embodiment, there is provided a single reaction line to effect an analysis for a single test item. As a reaction vessel use is made of a U-shaped tube 11 having large and small mouth portions 11a and 11b. On a turntable 12 are arranged equidistantly twenty four U-shaped tubes 11 along a periphery of the turntable. The turntable 12 is intermittently rotated in a direction shown by an arrow a at a given period of, for example 15 seconds, while the U-shaped tubes 11 are dipped into a thermostat 10 (see FIG. 4). Positions at which the U-shaped tubes 11 are stopped due to the stepwise rotation of the turntable 12 are denoted as $S_1$ to $S_{24}$. Hereinafter, the term "pitch" denotes the angular distance increment between adjacent ones of the equidistantly spaced vessels 11 on the turntable 12. In the present embodiment, into a U-shaped tube 11 positioned at $S_1$ is delivered a sample from a sample cup 15 which is situated just at a sample sucking position of a sampler 14 by means of a sample delivery device 13. The sampler 14 holds twenty four sample cups 15 arranged equidistantly along a disc which is rotated in a direction b in synchronism with the rotation of the turntable 12. In a U-shaped tube 11 in $S_3$ is selectively delivered an enzyme reagent 17 corresponding to substances in samples to be tested, by means of a reagent delivery device 16. In a U-shaped tube 11 situated at $S_4$ is poured a color reagent 19 with the aid of a reagent delivery device 18. Into a U-shaped reaction tube 11 is supplied a carrier 21 such as a synthetic resin particle or glass bead from a carrier supply device 21. It should be noted that the carrier 21 has a diameter smaller than an inner diameter of the large mouth portion 11a of the U-shaped tube 11, but is larger than an inner diameter of the small mouth portion 11b. On an outer surface of the carrier 21 there has been previously fixed antibody or antigen which causes the antigen-antibody reaction with antigen or antibody substance in the sample to be tested. Further, in the carrier supply device 20, the carriers 21 are wetted with a buffer solution. A reaction liquid in a U-shaped tube 11 at a position $S_{19}$ is sucked into a colorimeter 22, and a carrier 21 contained in a U-shaped tube 11 at a position $S_{20}$ is removed therefrom by means of a carrier discharge device 23. Into a U-shaped tube 11 at a position $S_{22}$ is supplied a washing liquid such as ion exchange water, buffer solution for immunological analysis, physiological saline solution, etc. In a U-shaped tube situated at a position $S_{24}$ is selectively delivered a buffer solution 26 by means of a buffer solution delivery device 25. At positions $S_2$ to $S_5$, a stirring air pump 27 can be detachably connected to small mouth portions 11b of U-shaped tubes 11, and at positions $S_{22}$ and $S_{23}$, a discharge pump 28 can be detachably connected to small mouth portions 11b of U-shaped tubes 11.

Now, the operation of the automatic analyzer shown in FIG. 3 will be explained also with reference to FIGS. 4A to 4D.

Figure 4A:
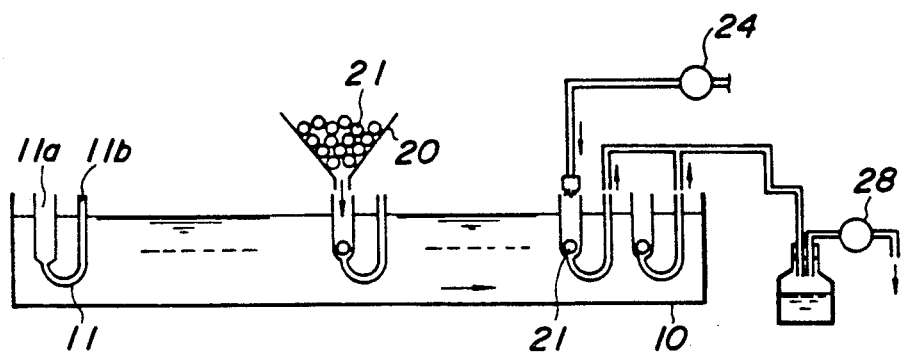
FIGS. 4A to 4D are schematic views showing an operation of the automatic analyzer shown in FIG. 3.

During a first revolution of the turntable 12, at the position $S_{17}$, a carrier 21 wetted with the buffer solution is supplied in a U-shaped tube 11 via its large mouth portion 11a as shown in FIG. 4A. Then, at the position $S_{22}$, the washing liquid is intermittently poured into the U-shaped tube 11 from the large mouth portion 11a just like a shower by means of the washing pump 24 and at the same time, the washing liquid is sucked out of the tube 11 via the small mouth portion 11b by means of the discharge pump 28. Next, at the position $S_{23}$, any washing liquid remaining in the tube 11 is discharged by the discharge pump 28. In this manner, the U-shaped reaction tube 11 is washed and at the same time, the buffer solution on the carrier 21 is removed. This ensures that an amount of the buffer solution 26 to be supplied by the buffer solution delivery device 25 can be made to be a given constant value.

Figure 4B:
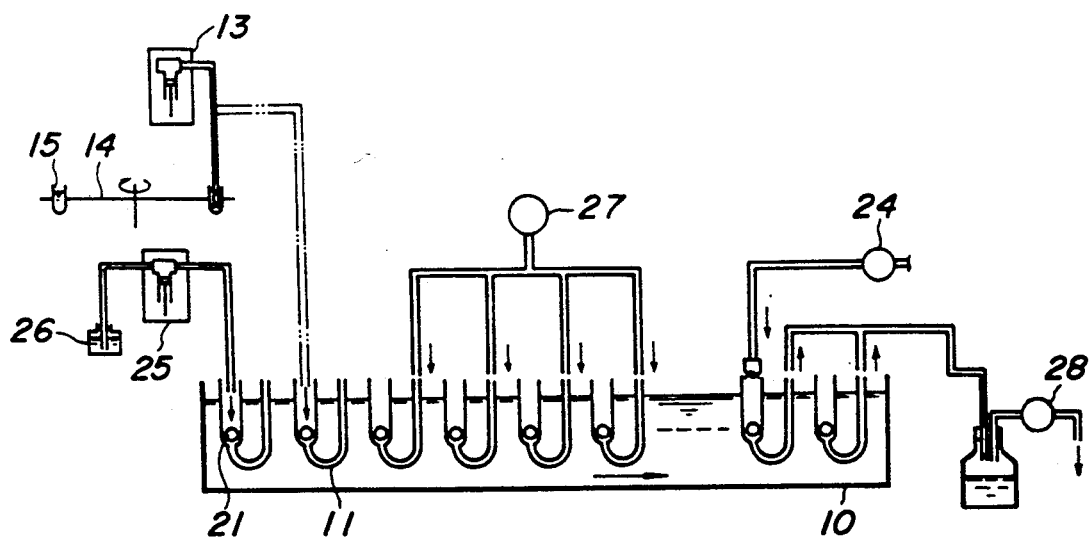

Then, as illustrated in FIG. 4B, at the position $S_{24}$ a given amount of the buffer solution 26 is delivered into the U-shaped tube 11 via its large mouth portion 11a by means of the delivery device 25. Then, at the position $S_1$ a given amount of a sample is delivered by means of the sample delivery device 13 into the tube 11 via its large mouth portion 11a from a sample cup 15 situated at the sample sucking position of the sampler 14. Next, at the positions $S_2$, $S_3$, $S_4$ and $S_5$, air streams are supplied into the U-shaped tube 11 from its small mouth portion 11b by means of the air pump 27 to stir the buffer solution and sample in the tube 11. In this manner, a first antigen-antibody reaction is caused to proceed. It should be noted that the carrier supply device 13 and sampler 14 are made inoperative after being once operated for respective U-shaped tubes.

Figure 4C:
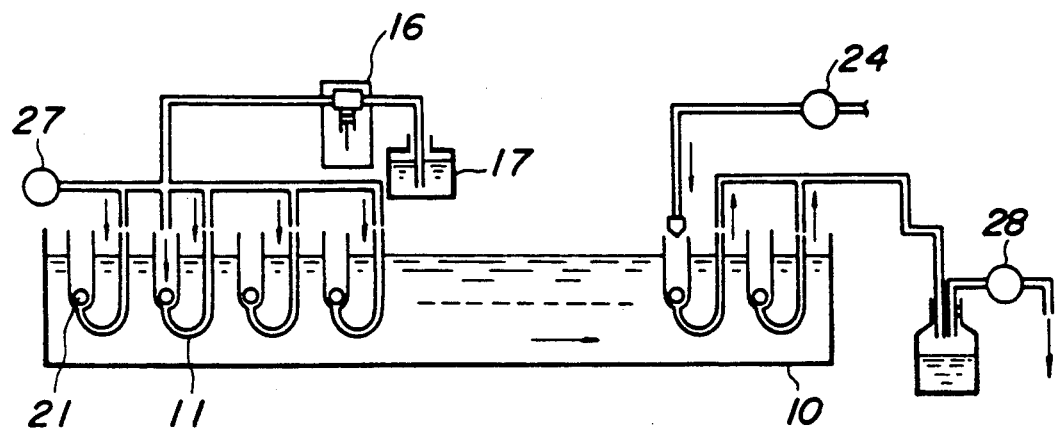

During a second revolution of the turntable 12, at the position $S_{22}$, the liquid in the tube 11 is sucked via the small mouth portion 11b by the discharge pump 28 and at the same time, the washing liquid is intermittently poured into the tube via its large mouth portion 11a by means of the washing pump 24. The washing liquid remaining in the tube is discharged at the positions $S_{22}$ and $S_{23}$ as shown in FIG. 4B. In this manner, the U-shaped tube 11 and the carrier 21 contained therein are fully washed to effect a first B-F separation. Then, at the position $S_3$, a given amount of the enzyme-labeled reagent 17 is delivered into the U-shaped tube 11 via its large mouth portion 11a by the reagent delivery device 16 as illustrated in FIG. 4C. The reagent and carrier are stirred sufficently at the positions $S_3$, $S_4$ and $S_5$ by supplying the air streams from the small mouth portion 11b with the aid of the air pump 27 to effect a second antigen-antibody reaction.

Figure 4D:
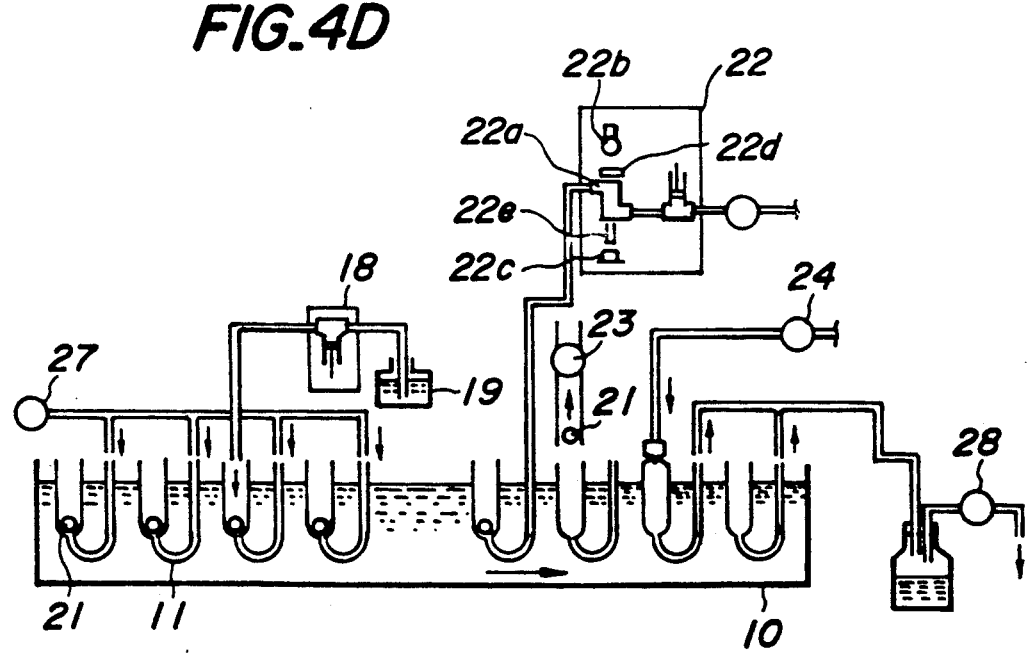

During a third revolution of the turntable 12, at the positions $S_{22}$ and $S_{23}$, the U-shaped tube 11 and carrier are washed by means of the washing pump 24 and discharge pump 28 to perform a second B-F separation. Next, as shown in FIG. 4D, a given amount of the color reagent 19, i.e. the enzyme substrate reagent, is delivered into the U-shaped tube 11 by the reagent delivery device 18. Then, the color reagent and carrier are stirred by means of the air pump 27 to produce a reaction of the color reagent 19 with the labeling enzyme of the enzyme-labeled reagent 17 bound with the carrier 21.

In a fourth revolution of the turntable 12, at the position $S_{19}$ a reaction liquid in the U-shaped tube 11 is sucked into the colorimeter 22 to effect the colorimetric measurement. As depicted in FIG. 4D, the colorimeter 22 comprises a flow cell 22a through which the reaction liquid is flown, and light source 22b and detector 22c arranged on respective sides of the flow cell 22a. Light emitted from the light source 22b is projected into the flow cell 22a via an interference filter 22d and light transmitted through the flow cell 22a is received by the detector 22c by means of a light guide 22e.

At the position $S_{20}$, the carrier 21 is sucked out of the U-shaped tube 11 via its large mouth portion 11a by the carrier discharge device 23. At the position $S_{22}$, the washing liquid is supplied into the U-shaped tube 11 via its large mouth portion 11a like a shower and the wash liquid is sucked out of the tube via its small mouth portion 11b. The wash liquid remaining in the tube is discharged at the position $S_{23}$. In this manner, the U-shaped tube 11 is prepared for a next supply of a carrier.

As explained above in detail, in the present embodiment since the U-shaped reaction tube 11 is repeatedly passed through the washing device comprising the washing pump 24 and discharge pump 28 to effect the washing including the B-F separation repeatedly, the whole analyzer can be made small in size and simple in construction.

Figure 5:
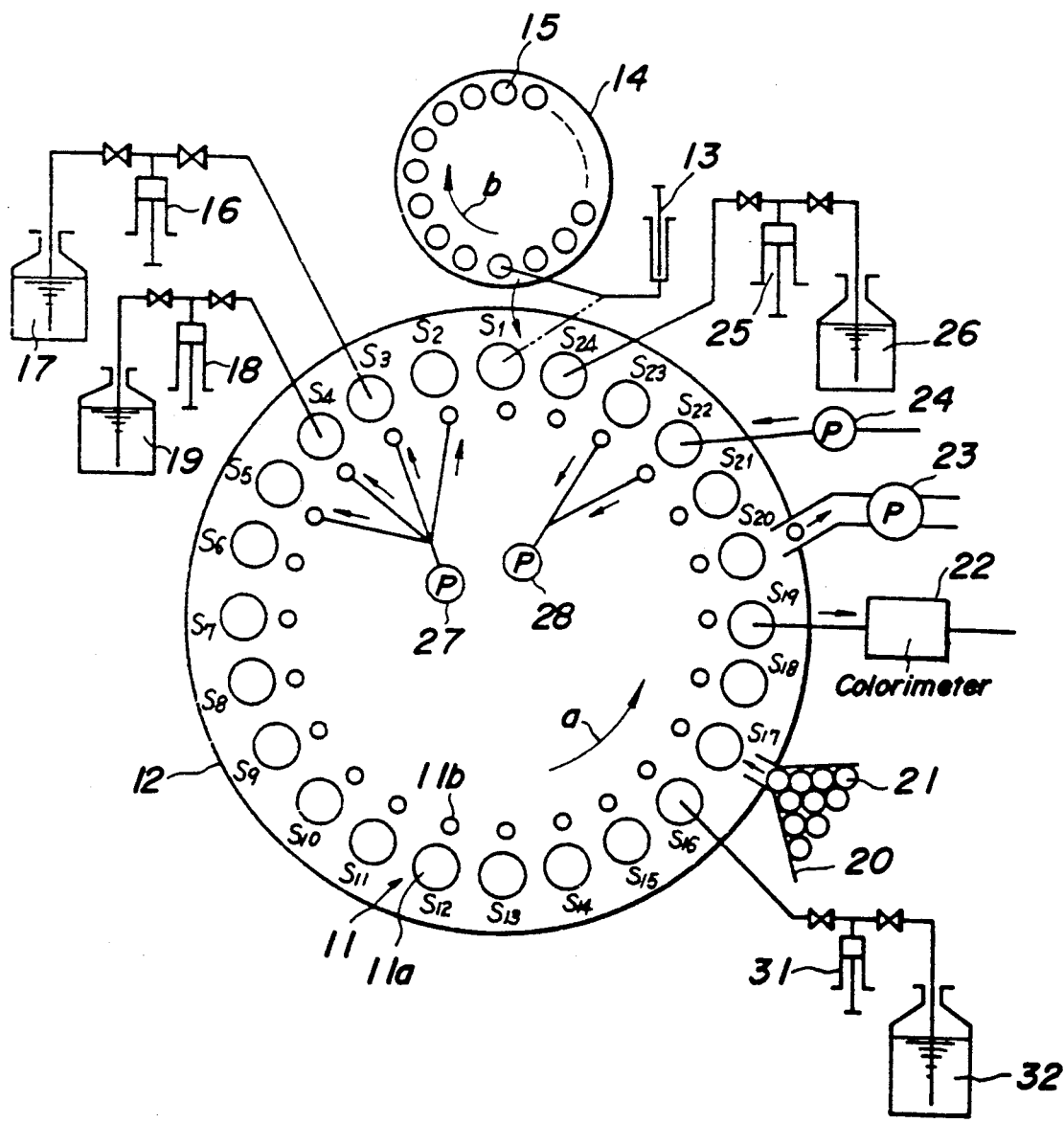
FIGS. 5 and 6 are schematic views showing another embodiment of the enzyme-immuno-assay automatic analyzer according to the invention.

FIG. 5 is a schematic view showing another embodiment of the automatic analyzer for effecting the enzyme-immuno-assay according to the invention. Portions similar to those shown in FIG. 3 are denoted by the same reference numerals used in FIG. 3. In the present embodiment, prior to the supply of a carrier 21 into a U-shaped tube 11, a given amount of a buffer solution 32 has been delivered into the tube at a position $S_{16}$ by means of a second buffer solution delivery device 31. The remaining construction and operation are entirely the same as those of the previous embodiment shown in FIG. 3. When the buffer solution 32 has been delivered into the tube 11, the carrier 21 can be supplied into the tube at the position $S_{17}$ with a minimum shock. It should be noted that it is not necessary to control precisely the delivery amount of the buffer solution 32, because the U-shaped tube 11 and carrier 21 are washed at the position $S_{22}$.

Figure 6:
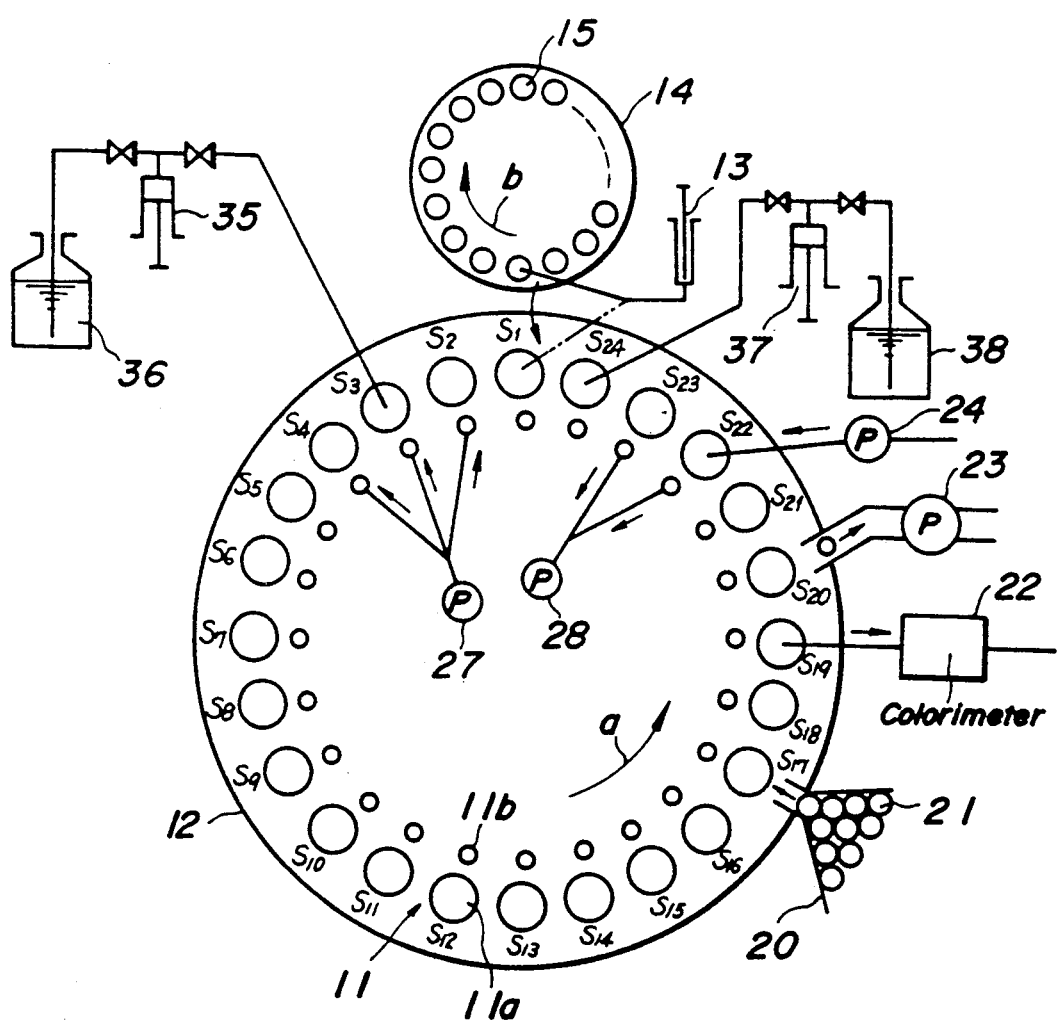

FIG. 6 is a schematic view illustrating an embodiment of the automatic analyzer according to the invention, in which the enzyme-immuno-assay is performed by the competitive method. Also in the present embodiment portions similar to those shown in FIG. 3 are denoted by the same reference numerals used in FIG. 3. In this embodiment, the delivery of the color reagent at the position $S_4$ and the mixing at the position $S_5$ are removed. At the position $S_3$, a given amount of a color reagent 36 instead of the enzyme-labeled reagent is delivered by means of a reagent delivery device 35 and at the position $S_{24}$, a given amount of an enzyme-labeled reagent 38 instead of the buffer solution is delivered by an enzyme-labeled reagent delivery device 37, said enzyme-labeled reagent 38 is prepared by marking with enzyme the same substance as that in a sample to be analyzed. The remaining construction of the analyzer in the present embodiment is entirely the same as that of the embodiment illustrated in FIG. 3.

Now the operation of the enzyme-immuno-assay automatic analyzer illustrated in FIG. 6 will be explained in detail also with reference to FIGS. 7A to 7C.

Figure 7A:
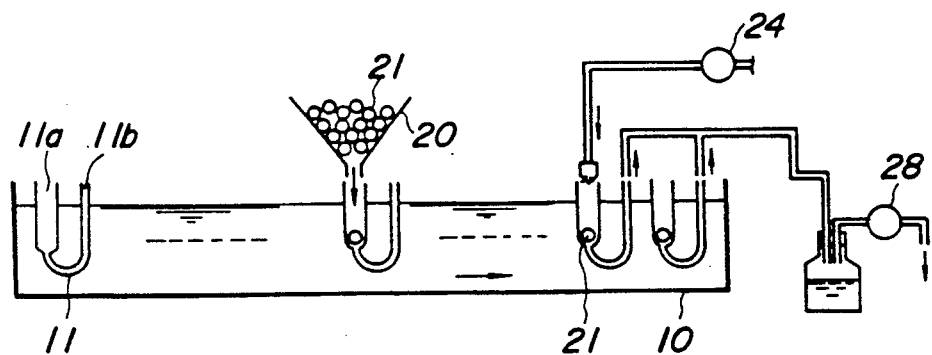
FIGS. 7A to 7C are schematic views illustrating an operation of the automatic analyzer shown in FIG. 6.
Figure 7B:
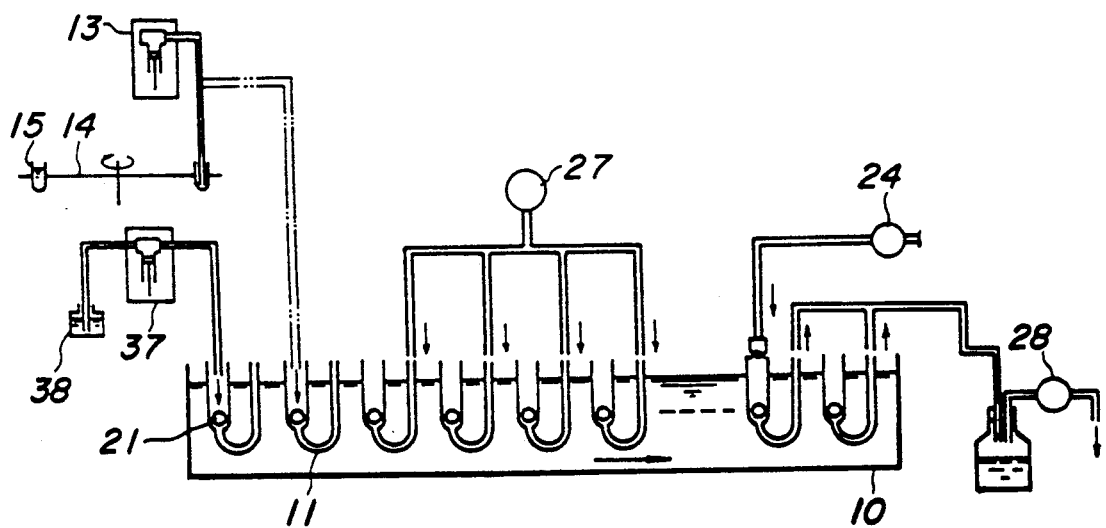

During the first revolution of the turntable 12, at the position $S_{17}$, a carrier 21 wetted with the buffer solution is supplied from the carrier supply device 20 into a U-shaped tube 11 as shown in FIG. 7A. Then, at the position $S_{22}$, the washing liquid is poured intermittently into the tube 11 like a shower by the washing pump 24 and the washing liquid remaining in the tube 11 is sucked out of the tube at the position $S_{23}$ by means of the discharge pump 28 via the small mouth portion 11b of the U-shaped tube. Next, as illustrated in FIG. 7B, at the position $S_{24}$ a given amount of the enzyme-labeled reagent 38 is delivered into the U-shaped tube 11 from its large mouth portion 11a by means of the reagent delivery device 37 and then at the position $S_1$, a given amount of a sample in a sample cup 15 in the sampler 14 is delivered into the U-shaped tube 11. Next, at the positions $S_2$ to $S_4$ the air streams are flown through the U-shaped tube 11 from its small mouth portion 11b to its large mouth portion 11a with the aid of the air pump 27 to mix the carrier 21, enzyme-labeled reagent 38 and sample with one another to produce the antigen-antibody reaction. It should be noted the carrier supply device 20, reagent delivery device 37, sample delivery device 13 and sampler 14 are kept inoperative once being operated for respective U-shaped tubes.

During a second revolution of the turntable 12, at the position $S_{22}$ the reaction liquid in the U-shaped tube 11 is sucked out of the tube by the discharge pump 28 and at the same time, the washing liquid is poured into the tube 11 and the washing liquid remaining in the tube 11 is discharged at the positions $S_{22}$ and $S_{23}$ by the pump 28 to effect the B-F separation.

Figure 7C:
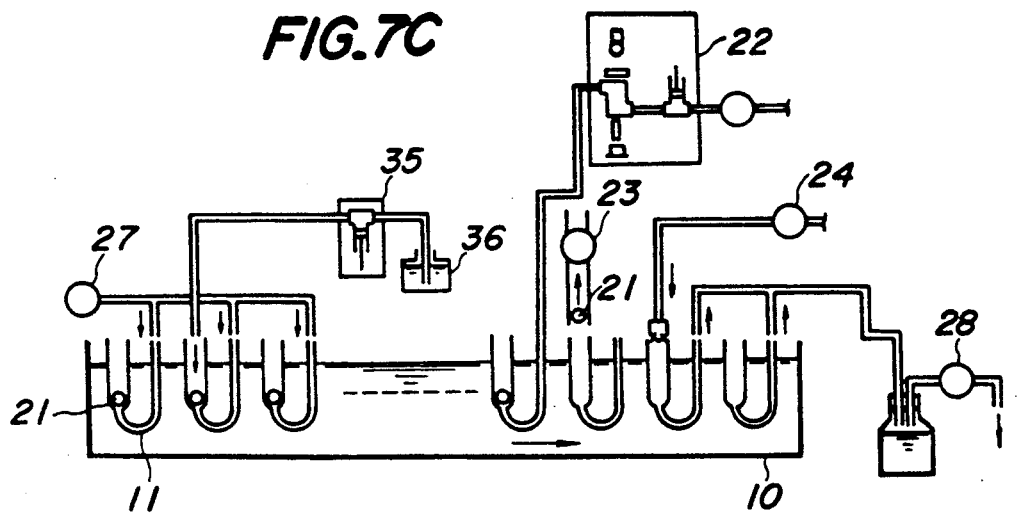

Then, as shown in FIG. 7C, at the position $S_3$ a given amount of the color reagent 36 is delivered by the reagent delivery device 35 into the U-shaped tube 11. Next, at the positions $S_3$ and $S_4$ the air streams are passed through the tube with the aid of the air pump 27 to stir the carrier 21 and color reagent 36 to produce the reaction.

In a third revolution of the turntable 12, at the position $S_{19}$ the reacted liquid in the U-shaped tube 11 is sucked into a flow cell of the colorimeter 22 to effect the colorimetric measurement. Next, at the position $S_{20}$ the carrier 21 contained in the tube 11 is withdrawn via the large mouth portion 11a by means of the carrier discharge device 23. At the position $S_{22}$, the washing liquid shower is intermittently supplied into the U-shaped tube 11 by the washing pump 24 and at the same time, the washing liquid is discharged through the small mouth portion 11b by means of the discharge pump 28. The washing liquid remaining in the tube 11 is discharged at the position $S_{23}$ by the pump 28. In this manner, the U-shaped tube 11 is washed effectively for preparing the analysis of another sample.

Also in the present embodiment, the reaction line is formed as an endless line and the U-shaped tubes 11 are repeatedly passed through the washing device comprising the washing pump 24 and discharge pump 28 to effect the washing including the B-F separation by a plurality of times. Therefore, the whole analyzer can be made small, simple and cheap.

In the above embodiments shown in FIGS. 3, 5 and 6, the number of the sample cups 15 held in the sampler 14 is made equal to that of the U-shaped tubes 11 supported by the turntable 12, and thus in case of analyzing samples the number of which is larger than that of the sample cups in the sampler 14, after the completion of the analysis for the samples in the sampler 14, a new set of samples must be set in the sampler 14. Therefore, the operator is subjected to cumbersome and time consuming work.

Figure 8:
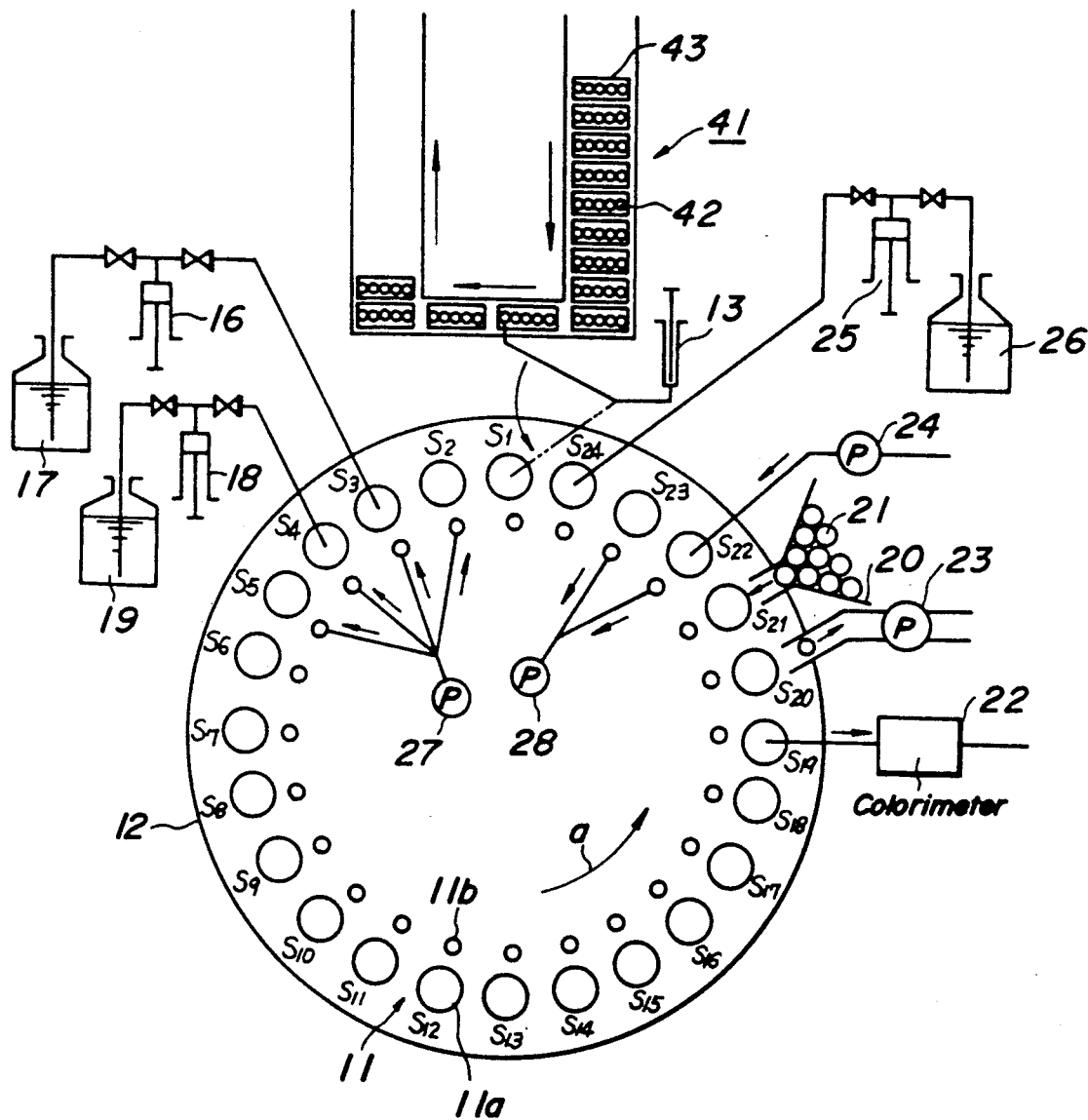
FIGS. 8 to 10 are schematic views depicting still another embodiments of the enzyme-immuno-assay automatic analyzer according to the invention.

FIG. 8 is a schematic view showing another embodiment of the enzyme-immuno-assay automatic analyzer according to the invention, in which the above mentioned drawbacks are obviated. The present embodiment differs from the embodiment shown in FIG. 3 only in the carrier supply position and the construction of a sampler 41. That is to say, a carrier 21 is supplied by the carrier supply device 20 into a U-shaped tube 11 at a position $S_{21}$ between the carrier discharge position $S_{20}$ and the washing position $S_{22}$. Further, the sampler 41 can hold a number of racks 43 each supporting a number of sample cups 42 and the racks 43 are successively transported along a substantially U-shaped path, while successive sample cups 42 are indexed at a sample sucking position.

In the present embodiment, after samples are delivered into all the U-shaped tubes 11 held in the turntable 12, the transportation of the racks 43 in the sampler 41 is once interrupted. As explained above with reference to FIG. 3, during a plurality of rotations of the turntable 12, the B-F separation has been effected twice, the test liquid has been sucked into the colorimeter 22 to effect the colorimetric measurement, the carrier 21 has been removed from the U-shaped tube 11, a new carrier 21 has been dropped into the U-shaped tube 11, and the washing and delivery of buffer solution 26 have been performed. Then, the transportation of the racks 43 in the sampler 41 is started again and twenty four samples are successively delivered into successive twenty four U-shaped tubes 11 on the turntable 12.

In the present embodiment, it is possible to set a large number of sample cups 42 larger than the number of the U-shaped tubes 11 onto the sampler 41, the labour work of the operator for setting the samples into the sampler 41 can be saved materially. Further, since the carrier supply position $S_{21}$ is set between the carrier discharge position $S_{20}$ and the washing position $S_{22}$, the washing of the U-shaped tubes which have been used for the analysis of samples can be performed simultaneously with the washing of the carriers 21 and thus, the processing speed can be increased as compared with the previous embodiments.

Figure 9:
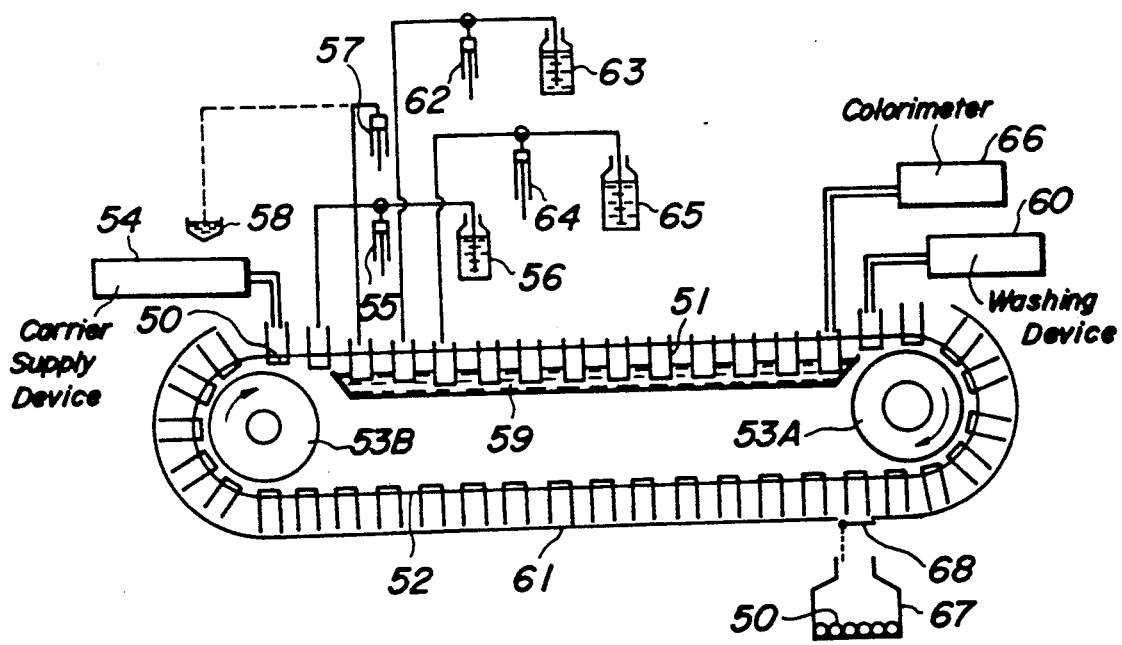

FIG. 9 is a schematic view depicting still another embodiment of the enzyme-immuno-assay automatic analyzer according to the invention, in which the sandwich method is utilized. In the present embodiment, a number of reaction vessels 51 in the form of a test tube are arranged equidistantly along an endless belt 52 which is intermittently rotated at a given pitch in a vertical plane by means of a pair of driving rollers 53A and 53B.

In the present embodiment, a carrier having given antibody or antigen fixed thereon is supplied into a reaction tube 51 by means of a carrier supply device 54. Next, a given amount of a buffer solution 56 is delivered into the tube 51 by a buffer solution delivery device 55. Then, a given amount of a sample contained in a sample cup 58 is further delivered into the tube 51 by means of a sample delivery device 57 to initiate the first antigen-antibody reaction, while the reaction tube 51 is immersed in a thermostat 59. The carrier supply device 54, buffer solution delivery device 55 and sample delivery device 57 are once kept inoperative after the given number of operations corresponding to the number of the reaction tubes or samples has been finished. At the end of the thermostat 59, the reaction tube 51 and carrier 50 are washed by a washing device 60 to effect a first B-F separation. Then the reaction tube 51 is turned up-side-down, while the carrier 50 caused to remain in the tube. To this end, along the travelling path of the reaction tube there is arranged a member 61 for preventing the carrier 50 from being dropped off the reaction tube 51. This member 61 may be formed by a mesh.

During a second revolution of the endless belt 52, a given amount of an enzyme-labeled reagent 63 is delivered into the reaction tube 51 by a reagent delivery device 62 to start a second antigen-antibody reaction, while the tube 51 is transported through the thermostat 59. Then the carrier 50 and tube 51 are washed by the washing device 60 to effect a second B-F separation. In a third revolution of the endless belt 52, a given amount of a color reagent 65 is delivered into the reaction tube 51 with the aid of a second reagent delivery device 64. After a given reaction has been completed, a test liquid in the reaction tube 51 is sucked into a colorimeter 66 to effect a colorimetry. After that, the reaction tube 51 is washed again by the washing device 60 and the carrier 50 is dropped off the reaction tube 51 via a swingable gate 68 into a waste carrier container 67.

In the present embodiment, the endless reaction line is formed in the vertical plane and a plurality of washings including the B-F separation are carried out by means of the single washing device 60 and therefore, the whole apparatus can be made small in size, simple in construction and cheap in cost.

Figure 10:
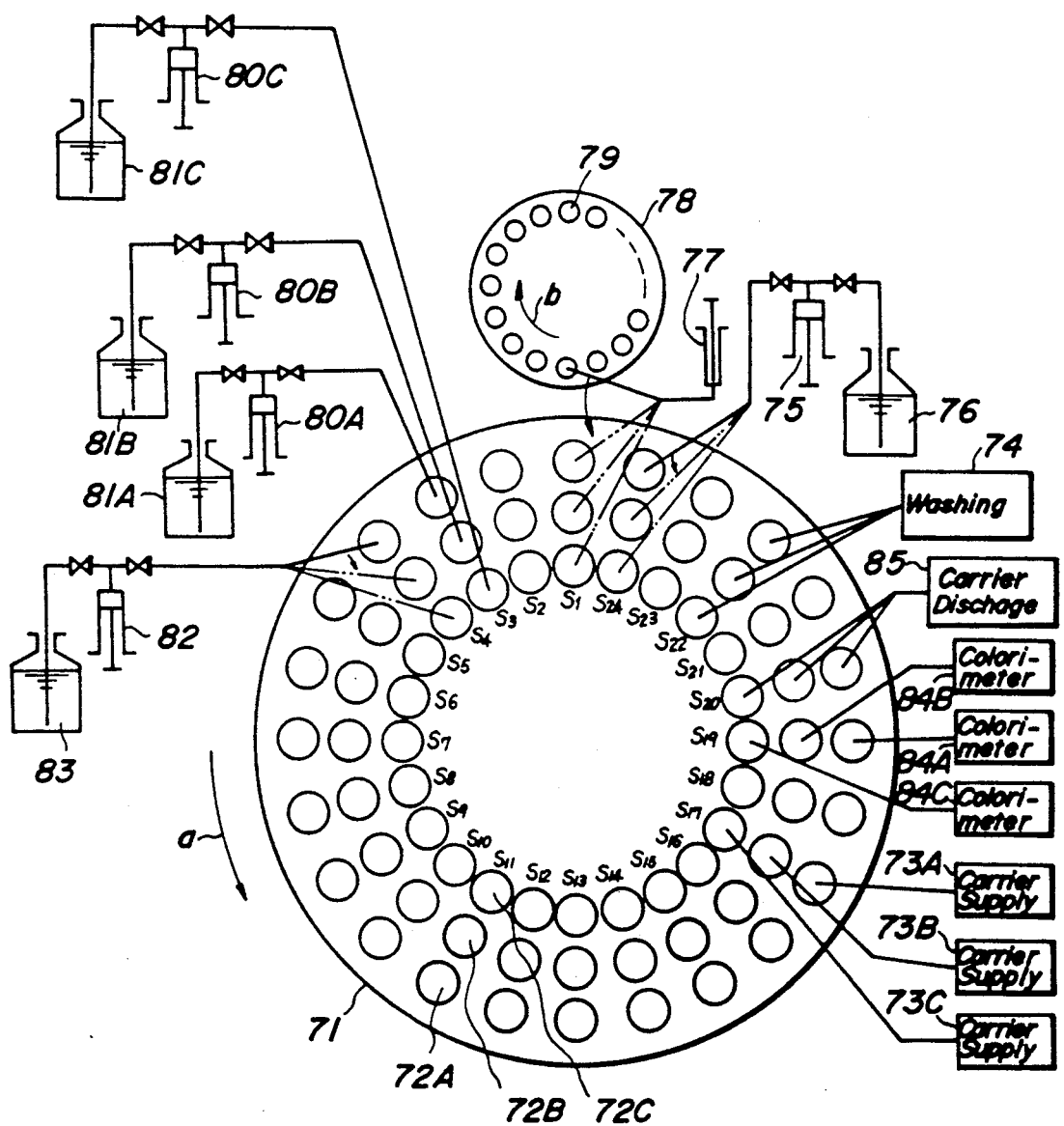

FIG. 10 is a schematic view showing still another embodiment of the automatic analyzer according to the invention in which three test items are analyzed for respective samples by means of the sandwich method. On a turntable 71 rotating intermittently in a direction a are arranged concentrically three rows of reaction vessels, each including twenty four reaction vessels 72. As shown in FIG. 10, the reaction vessels 72 are arranged in a radial manner. The successive analyzing steps for respective reaction vessels 71 are the same as those explained above in the embodiment shown in FIG. 3 and thus will be explained briefly hereinbelow. At a position $S_{17}$, three carriers are supplied into three reaction vessels 72A, 72B and 72C belonging to respective rows by means of carrier supply devices 73A, 73B and 73C, respectively. Then at a position $S_{22}$, the reaction vessels and carriers contained therein are washed by a washing device 74 which comprises a wash liquid supplying and sucking mechanism. Next, at a position $S_{24}$, given amounts of a buffer solution 76 are delivered into the three reaction tubes 72A, 72B and 72C by a buffer solution delivery device 75. Further, at a position $S_1$, given amounts of a sample in a sample cup 79 in a sampler 78 are delivered via sample delivery device 77 into the three reaction vessels 72A, 72B and 72C to effect a first antigen-antibody reaction. It should be noted that given antibody or antigen corresponding to substances in a sample to be analyzed is fixed to the carriers, respectively.

During a second revolution of the turntable 71, the reaction vessels and carriers are washed at the position $S_{22}$ by the washing device 74 to perform a first B-F separation. Then, at a position $S_3$, enzyme-labeled reagents 81A, 81B and 81C corresponding to the respective test items are delivered into the reaction tubes 72A, 72B and 72C by means of reagent delivery devices 80A, 80B and 80C, respectively to effect a second antigen-antibody reaction. In a third rotation of the turntable 71, the reaction vessels and carriers are washed by the washing device 74 at the position $S_{22}$ to perform a second B-F separation. Then, given amounts of a color reagent 83 are delivered into the reaction tubes 72A, 72B and 72C by a second reagent delivery device 82. Next, test liquids in the reaction vessels 72A, 72B and 72C are sucked into colorimeters 84A, 84B and 84C, respectively to effect the colorimetric measurement. Finally, at a position $S_{20}$ the carriers remaining in the reaction vessels 72A, 72B and 72C are discharged by a carrier discharge device 85 and then at the position $S_{22}$ the reaction vessels 72A, 72B and 72C are washed by the washing device 74 to prepare the analysis for new samples.

In the present embodiment, a plurality of test items for respective samples can be analyzed simultaneously and thus, the processing ability of the analyzer becomes very high. Further, the reaction vessels are repeatedly indexed at the washing position $S_{22}$ and a plurality of washings including the B-F separation can be done by the single washing device 74. Therefore, the analyzer becomes small and simple, while the processing ability is very high.

Figure 11:
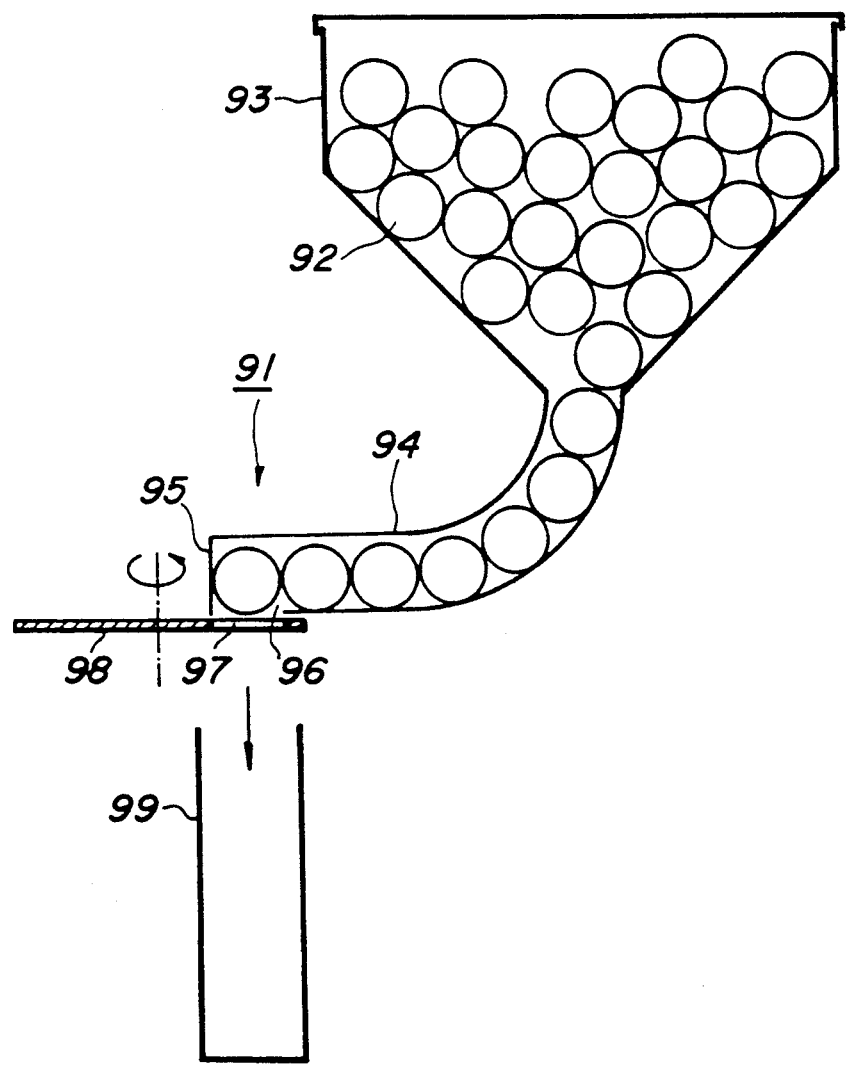
FIG. 11 is a side view showing an embodiment of a carrier supply device according to the invention.

FIG. 11 is a schematic side view depicting an embodiment of the carrier supply device for throwing a carrier into a reaction vessel. The carrier supply device 91 comprises a hopper 93 for holding a number of carriers 92. At a lower end of the hopper 93 is connected one end of a passage 94 having a curved portion and a linear portion. The carriers are rolled down into the duct 94 due to the gravitational force and are aligned therein. At the other end of the passage 94 is arranged a vertical wall 95 for limiting the horizontal movement of carriers and an outlet 96 is formed in a lower wall of the duct 94. Near the outlet 96 is rotatably arranged a disc 98 in which an opening 97 is formed. By suitably rotating the disc 98 the carriers 92 can be successively discharged from the duct 94 one by one via the outlet 96 and opening 97. The carrier supply device 91 of the present embodiment is simple and the carriers 92 can be positively supplied into a reaction vessel 99 one by one.

Figure 12:
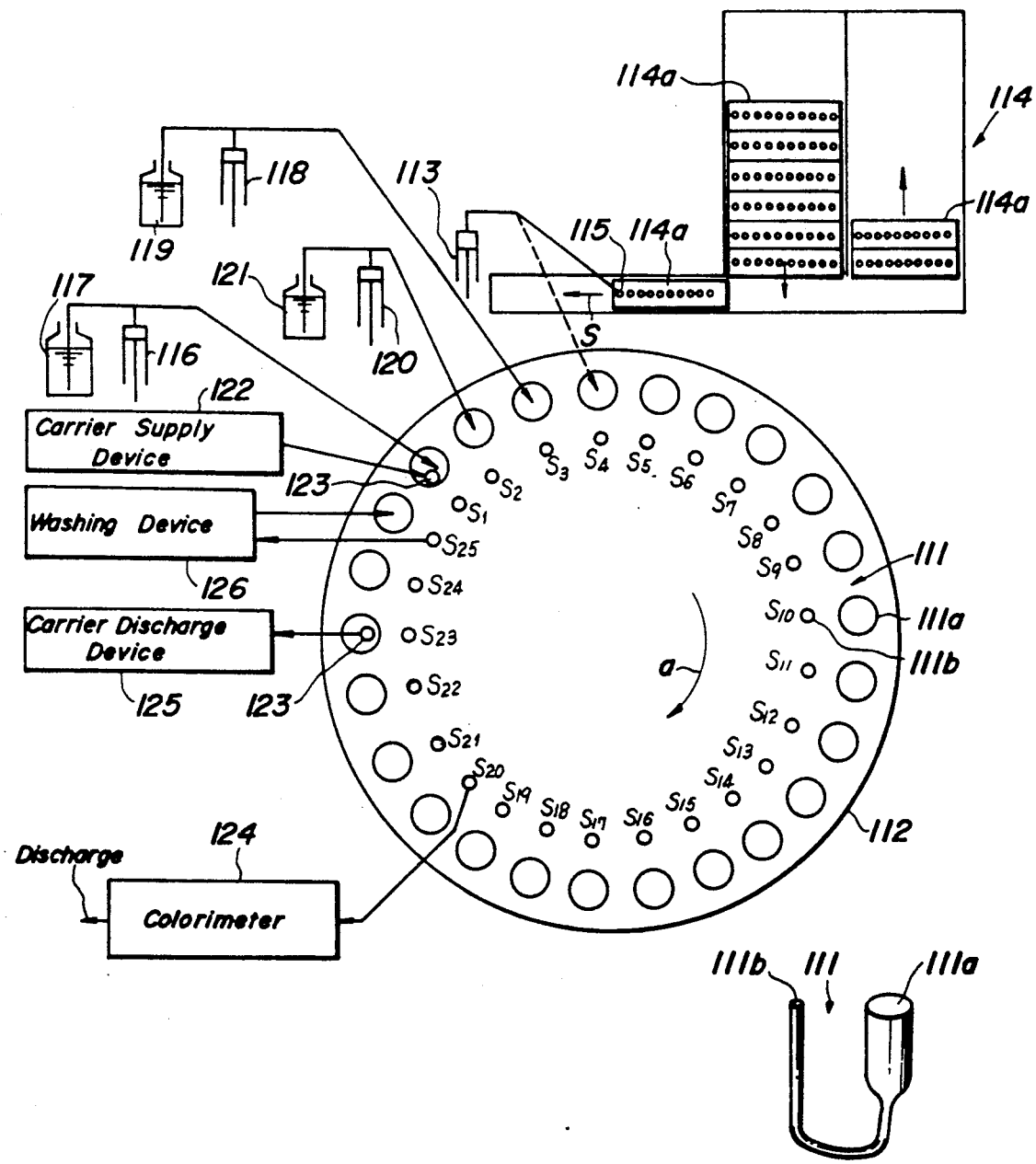
FIG. 12 is a schematic view illustrating still another embodiment of the enzyme-immuno-assay automatic analyzer according to the invention.
Figure 13A:
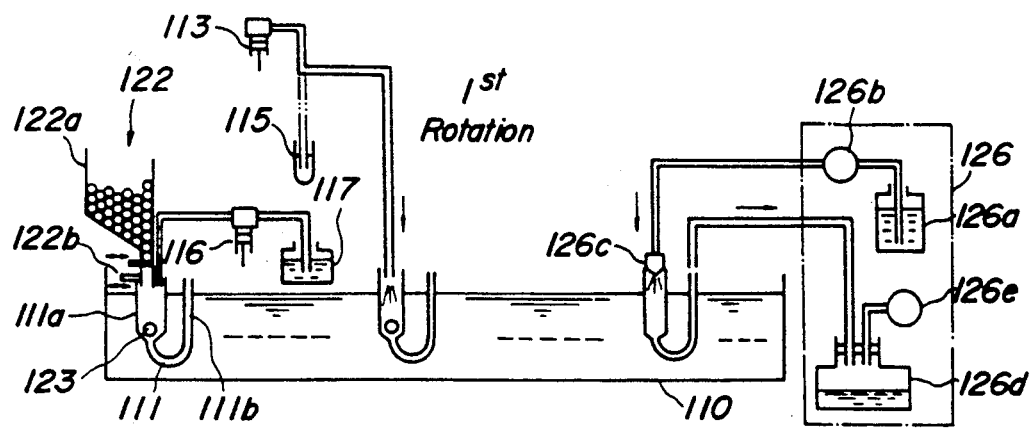
FIGS. 13A to 13C are schematic views depicting an operation of the automatic analyzer shown in FIG. 12.
Figure 13B:
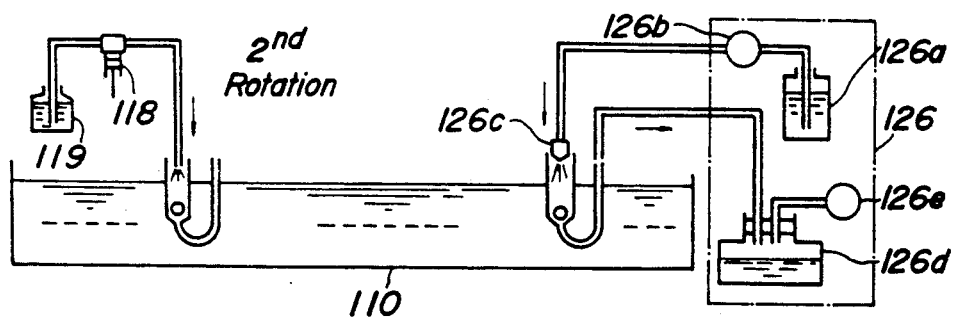
Figure 13C:
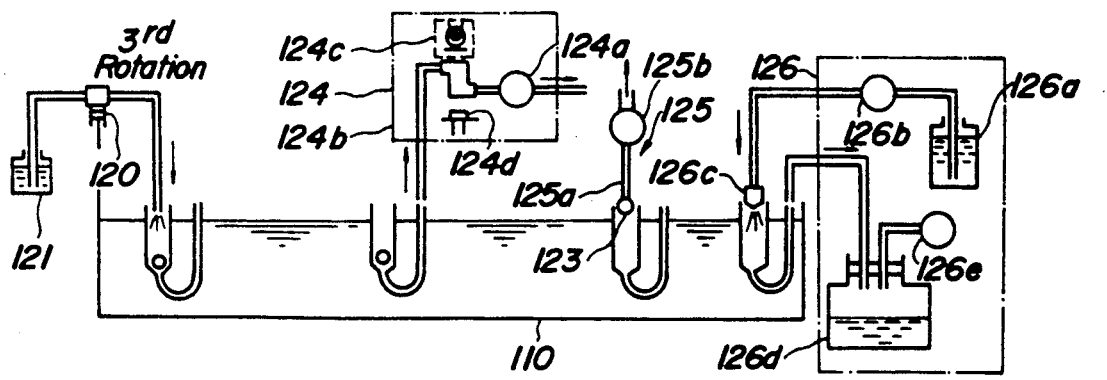

FIG. 12 is a schematic view showing another embodiment of the automatic enzyme-immuno-assay analyzer according to the invention, which utilizes the sandwich method shown in FIG. 2. In this embodiment, twenty five U-shaped tubes 111 each having a large mouth portion 111a and a small mouth portion 111b are used as a reaction vessel as shown in FIGS. 13A to 13C, and are arranged concentrically on a turntable 112 at a same interval. The turntable 112 functions to rotate intermittently the U-shaped tubes 111 in the direction of arrow a at a given period for example 15 seconds), while the U-shaped tubes are always immersed in a thermostat 110 as shown in FIGS. 13A to 13C. Stop positions of the U-shaped tube 111 caused by the intermittent rotation of the turntable 112 are denoted by marks $S_1$ to $S_{25}$. At the stop position $S_4$, the sample to be measured are selectively delivered into the U-shaped tube 111 from a sample cup 115 positioned at a predetermined sample suction position of a sampler 114 by means of a sample delivery device 113. As for the sampler 114, various types of samplers can be used. In this embodiment, the sampler 114 holds a plurality of racks 114a each having ten sample cups. As shown in FIG. 12, the racks 114a arranged in a left column in the sampler 114 are successively moved downward to the sample delivery position, and the racks 114a arranged in a right column in the sampler 114 are moved upward. The rack 114a positioned at the sample delivery position is moved intermittently in the direction of arrow S in synchronism with the rotation of the turntable 112. When the sample delivery operation for all the samples in the rack 114a is finished, this rack 114a is moved into the lower end of the right column of the sampler 114 and then the rack 114a positioned at the lowermost position of the left column is moved to the sample delivery position. In this manner, the samples to be measured can be successively transferred to the sample delivery position at a given pitch.

At the stop position $S_1$, a first reagent 117 is selectively delivered into the U-shaped tube 111 by means of a first reagent delivery device 116. As for the first reagent 117, use is made of a buffer solution. At the stop position $S_3$, an enzyme-labeled reagent 119 corresponding to the substance to be measured in the sample is selectively delivered into the U-shaped tube 111 by means of a second reagent delivery device 118. Further, at the stop position $S_2$, a color reagent 121 is selectively delivered into the U-shaped tube 111 by means of a third reagent delivery device 120. Furthermore, by utilizing a carrier supply device 122, one of insoluble carriers made of a synthetic resin such as plastics or a glass bead which are accommodated therein is selectively delivered into the U-shaped tube 111 through the large mouth portion 111a. A size of the carrier 123 is so determined as to be easily put in and out from the large mouth portion 111a and not to be inserted into the small mouth portion 111b, and to the surface of the carrier 123 is previously fixed an antigen or an antibody which causes an antigen-antibody reaction with the substance to be measured in the sample. Moreover, at the stop position $S_{20}$, a reaction liquid supplied in the U-shaped tube 111 is selectively sucked into a colorimeter 124, and also at the stop position $S_{23}$, the carrier 123 accommodated in the U-shaped tube 111 is selectively put out by means of a carrier discharge device 125. Furthermore, at the stop position $S_{25}$, a washing liquid such as an ion-exchange water, a buffer solution for an immunoanalysis and a physiological saline solution is selectively supplied into and then discharged from the U-shaped tube 111 by means of a washing device 126 so as to effect the B-F separation and to wash the U-shaped tube 111.

Hereinafter, an operation of the automatic enzyme-immuno-assay analyzer shown in FIG. 12 will be explained with reference to FIGS. 13A to 13C and 14A to 14I.

In this embodiment, since use is made of the sandwich method, the analysis for each of the samples caused to end within three rotations of the turntable 112. That is to say, the B-F separation is effected two times and the washing operation of the U-shaped tube is effected once, till the end of the analysis for each samples. Therefore, each of the sample delivery, the first, second, third reagent delivery, the carrier supply, the carrier discharge operations and the sucking operation into the colorimeter is effected every three pitches in the course of the rotation of the turntable 112. However, since the washing operation is effected three times till the end of the analysis for each of the samples as mentioned above, it is necessary to effect the washing operation every one pitch in the course of the rotation of the turntable 112. Moreover, in order to effect the operations mentioned above, it is necessary to arrange $3n+1$ or $3n+2$ number of U-shaped tubes 111 on the turntable 112, where $n=1, 2, 3 \ldots$. In this embodiment, the number of the U-shaped tubes 111 is twenty five and thus the requirement of $3n+1$ is satisfied at $n=8$.

In the course of the first rotation of the turntable 112, at first as shown in FIG. 13A, one carrier 123 is supplied into the U-shaped tube 111 positioned at the stop position $S_1$ through the large mouth portion 111a (FIG. 14C). Also at the stop position $S_1$, a predetermined amount of the first reagent 117 consisting of the buffer solution is delivered into the U-shaped tube 111 by means of the first reagent delivery device 116 (FIG. 14D). After this U-shaped tube 111 is transferred by three pitches, at the stop position $S_4$, a predetermined amount of the samples is delivered into the U-shaped tube 111 by means of the sample delivery device 113 (FIG. 14F). Then, the antigen-antibody reaction is initiated from this sample delivery operation. The U-shaped tube 111 reaches the stop position $S_{25}$ at the end of the first rotation, and at this stop position $S_{25}$ the washing operation for the U-shaped tube 111 is effected by the washing device 126 so as to perform the first B-F separation (FIG. 14B). In FIGS. 14B to 14I, the operational timings for the relevant sample are illustrated by hatching.

Next, in the course of the second rotation of the turntable 112, at the stop position $S_3$ a predetermined amount of the enzyme-labeled reagent 119 is delivered into the U-shaped tube 111 by means of the second reagent delivery device 118 to start the second reaction (FIG. 14F). At the last stop position $S_{25}$ during the second rotation, the second B-F separation is effected by the washing device 126 (FIG. 14B).

Further, in the course of the third rotation of the turntable 112, at the stop position $S_2$ a predetermined amount of the color reagent 121 is delivered into the U-shaped tube 111 by means of the third reagent delivery device 120 to start the third reaction (FIG. 14G). Then, at the stop position $S_{20}$, the test liquid in the U-shaped tube 111 is sucked by a pump arranged in the colorimeter 124 and is introduced into a colorimetry flow cell to effect the colorimetry thereof with a light having a predetermined wavelength (FIG. 14H). Next, at the stop position $S_{23}$ after three pitch rotations, the carrier 123 remaining in the U-shaped tube 111 is removed by means of the carrier discharge device 125 (FIG. 14I). At the last stop position $S_{25}$ during the third rotation, the U-shaped tube 111 is washed by the washing device 26 and is used repeatedly for the analysis of the next sample. In FIGS. 14C to 14E, the operational timings for the next sample to be measured are illustrated by cross hatching.

The washing operation by utilizing the washing device 126 is so performed that the washing liquid is intermittently supplied into the U-shaped tube 111 through the large mouth portion 111a in a shower mode and is discharged from the small mouth portion 111b by means of a liquid discharge pump. As shown in FIGS. 13A to 13C, the washing device 126 comprises a washing liquid tank 126a, a washing liquid supply pump 126b, a nozzle 126c, a liquid discharge tank 126d and a liquid discharge pump 126e. Moreover, as shown in FIG. 13A, the carrier supply device 122 comprises a hopper 122a for accommodating a plurality of carriers 123 and a gate device 122b for supplying the carrier 123 one by one from the hopper 122a. Generally, the carriers 123 are held in the hopper 122a and are wetted with the buffer solution. Further, as shown in FIG. 13C, the carrier discharge device 125 functions to descend a nozzle 125a into the large mouth portion 111a so as to put out the carrier 123 by sucking it through the nozzle, or to descend an arm into the large mouth portion so as to put out the carrier by holding it by fingers provided at an end of the arm.

In the embodiment mentioned above, since the sample delivery, the first, second, third reagent delivery, the carrier supply and discharge, the colorimetry operations are effected every three pitches, and the $3 \times 8 + 1 = 25$ number of U-shaped tubes 111 are arranged concentrically on the turntable 112 with the same interval therebetween, for example at the stop position $S_4$ the U-shaped tube 111 deviates by one pitch every one rotation of the turntable 112 viewed in the rotational direction of the turntable. Since the same can be applied to the operation which is performed every three pitches, the sample delivery operation is performed every three pitches. In this manner, the analysis for one sample is finished successively every three pitches. Therefore, it is possible to effect an ID control of the sample and the processing of the analytical result at a constant period, and thus various controls can be effected easily. Further, since use is made of an endless reaction line and the U-shaped tube 111 is transferred circularly for effecting the washing operation including the B-F separation repeatedly by means of one washing device 126 arranged in the reaction line, it is possible to make the whole apparatus small in size, simple in construction and inexpensive in cost.

Figure 15:
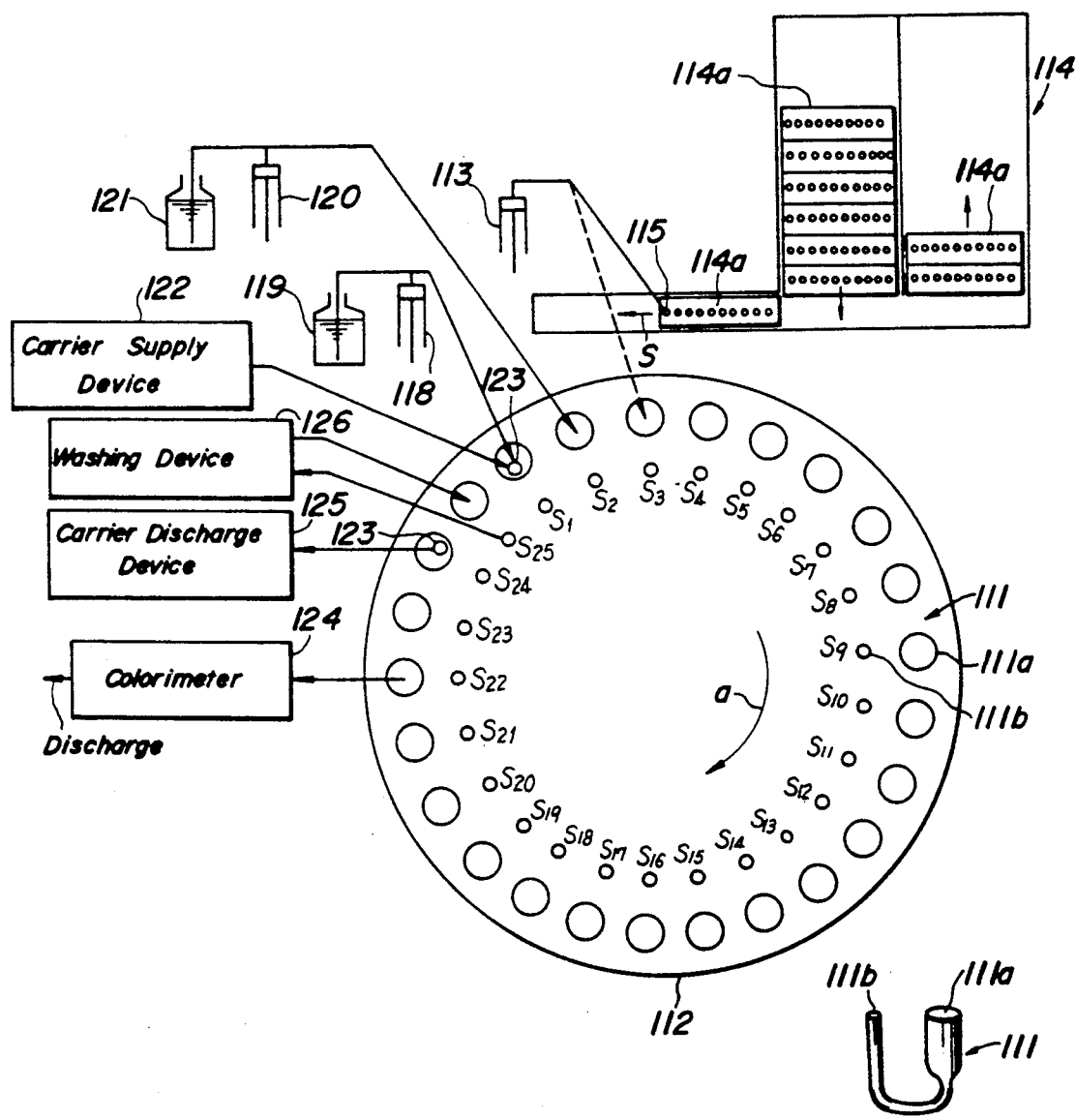
FIG. 15 is a schematic view showing still another embodiment of the enzyme-immuno-assay automatic analyzer according to the invention.

FIG. 15 is a schematic view showing another embodiment of the automatic enzyme-immuno-assay analyzer according to the invention, which utilizes the competitive method shown in FIG. 1, and FIGS. 16A to 16H are timing charts for explaining the operations of the analyzer shown in FIG. 15. Portions in FIG. 15 similar to those shown in FIG. 12 are denoted by the same reference numerals used in FIG. 12. As explained above with reference to FIG. 1, the competitive method needs two washing operations including the B-F separation. Therefore, in the embodiment shown in FIG. 15, the 2n+1 number of the U-shaped tubes 111 are arranged on the turntable 112, and the operations are so controlled that the sample delivery, the reagent delivery, the carrier supply and discharge, the colorimetry operations are effected every two pitches and the washing operation is effected every one pitch. In this manner, the sample delivery operation can be successively performed every two pitches.

In the embodiment shown in FIG. 15, at the stop position $S_1$ the first reagent 119 consisting of the enzyme-labeled reagent is delivered into the U-shaped tube 111 by means of the first reagent delivery device 118 and also one carrier 123 is supplied into the U-shaped tube 111 by means of the carrier supply device 122. Moreover, at the stop position $S_2$ the color reagent 121 is delivered into the U-shaped tube 111 by means of the second reagent delivery device 120. Further, at the stop position $S_3$ the sample is delivered into the U-shaped tube 111 by means of the sample delivery device 113. Also in this embodiment, the sample to be measured is transferred successively to the sample delivery position by means of the sampler 114 which accommodates a plurality of sample racks 114a each having a number of sample cups 115. As shown in FIG. 15, the U-shaped tube 111 which is utilized as the reaction vessel has the large mouth portion 111a and the small mouth portion 111b. At the stop position $S_{22}$, the test liquid in the U-shaped tube 111 is sucked into the colorimeter 124 to effect the colorimetry. Then, at the stop position $S_{24}$, the carrier 123 remaining in the U-shaped tube 111 is put out by means of the carrier discharge device 125, and also at the stop position $S_{25}$ the washing operation including the B-F separation is performed by means of the washing device 126.

In the timing charts shown in FIGS. 16A to 16H, first of all at the stop position $S_1$ one carrier 123 is supplied into the U-shaped tube 111 by means of the carrier supply device 122 as shown in FIG. 16C and also a predetermined amount of the enzyme-labeled reagent 119 is delivered into the U-shaped tube 111 by means of the first reagent delivery device 118 as shown in FIG. 16D. When the U-shaped tube 111 reaches the stop position $S_3$ after two pitch rotations, a predetermined amount of sample is delivered into the U-shaped tube 111 to start the antigen-antibody reaction as shown in FIG. 16E. Then, at the last stop position $S_{25}$ during the first rotation, the B-F separation is effected by means of the washing device 126 as shown in FIG. 16B. After proceeding by two pitches, at the stop position $S_2$ a predetermined amount of the color reagent 121 is delivered into the U-shaped tube 111 by means of the second reagent delivery device 120 to start the second reaction as shown in FIG. 16F. When the U-shaped tube 111 reaches the stop position $S_{22}$, the test liquid is sucked into the colorimetry flow cell by means of the colorimeter 124 to effect the colorimetry thereof as shown in FIG. 16G. After proceeding by two pitches, at the stop position $S_{24}$ the carrier 123 remaining in the U-shaped tube 111 is discharged by means of the carrier discharge device 125 as shown in FIG. 16H. At the last stop position $S_{25}$ during the second rotation, the empty U-shaped tube 111 is washed by the washing device 126 as shown in FIG. 16B to prepare the analysis for the next sample. In this manner, predetermined analyses for each of the samples can be performed within two rotations of the turntable 112. Moreover, in this embodiment, since the 2n+1 number of the U-shaped tubes 111 are arranged on the turntable 112, and the sample delivery, the reagent delivery, the carrier supply and discharge, the colorimetry operations are effected every two pitches, successive samples can be delivered at two pitch interval. However, the washing operation must be effected every one pitch.

Figure 17:
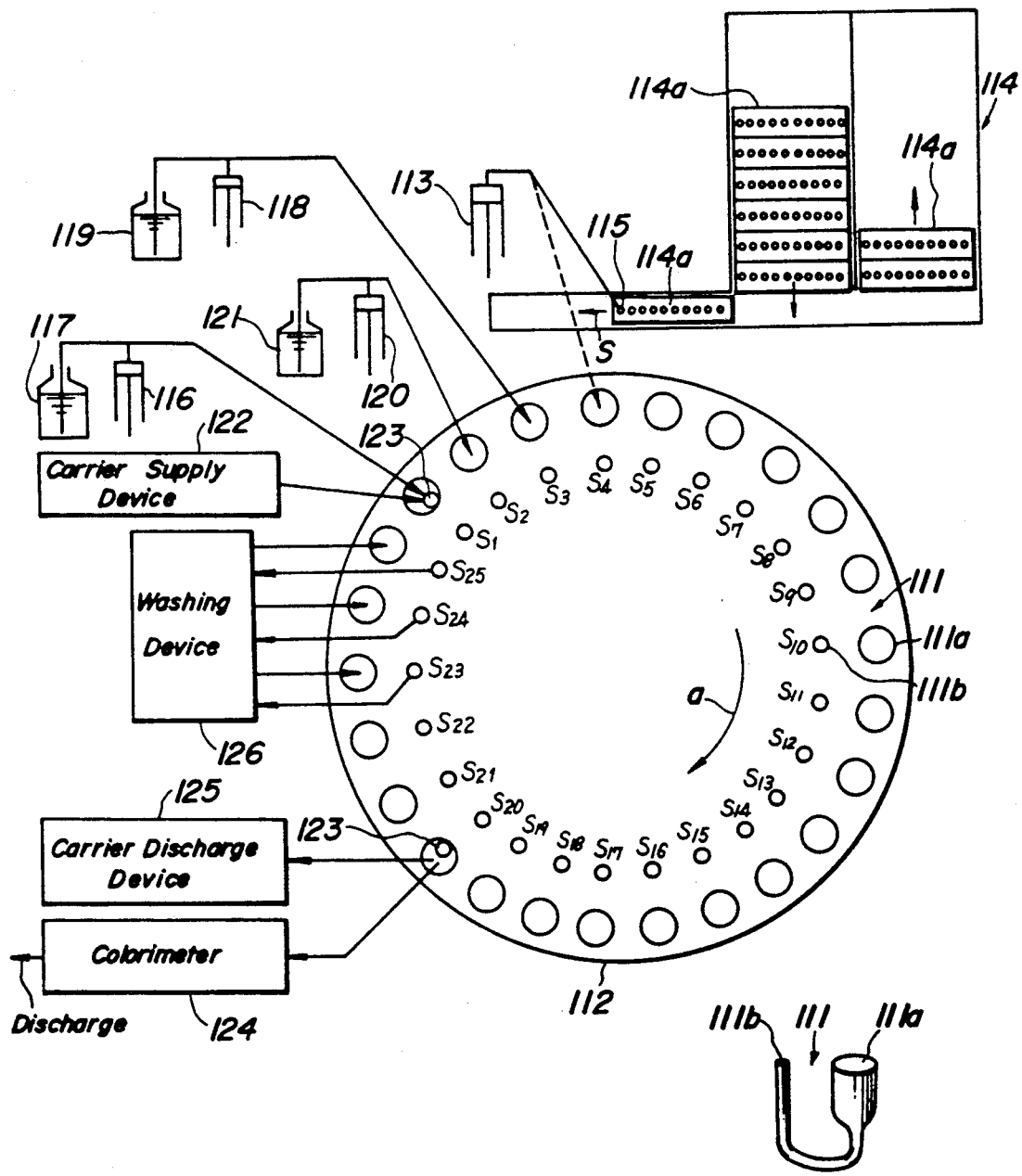
FIG. 17 is a schematic view illustrating still another embodiment of the enzyme-immuno-assay automatic analyzer according to the invention.
Figure 18:
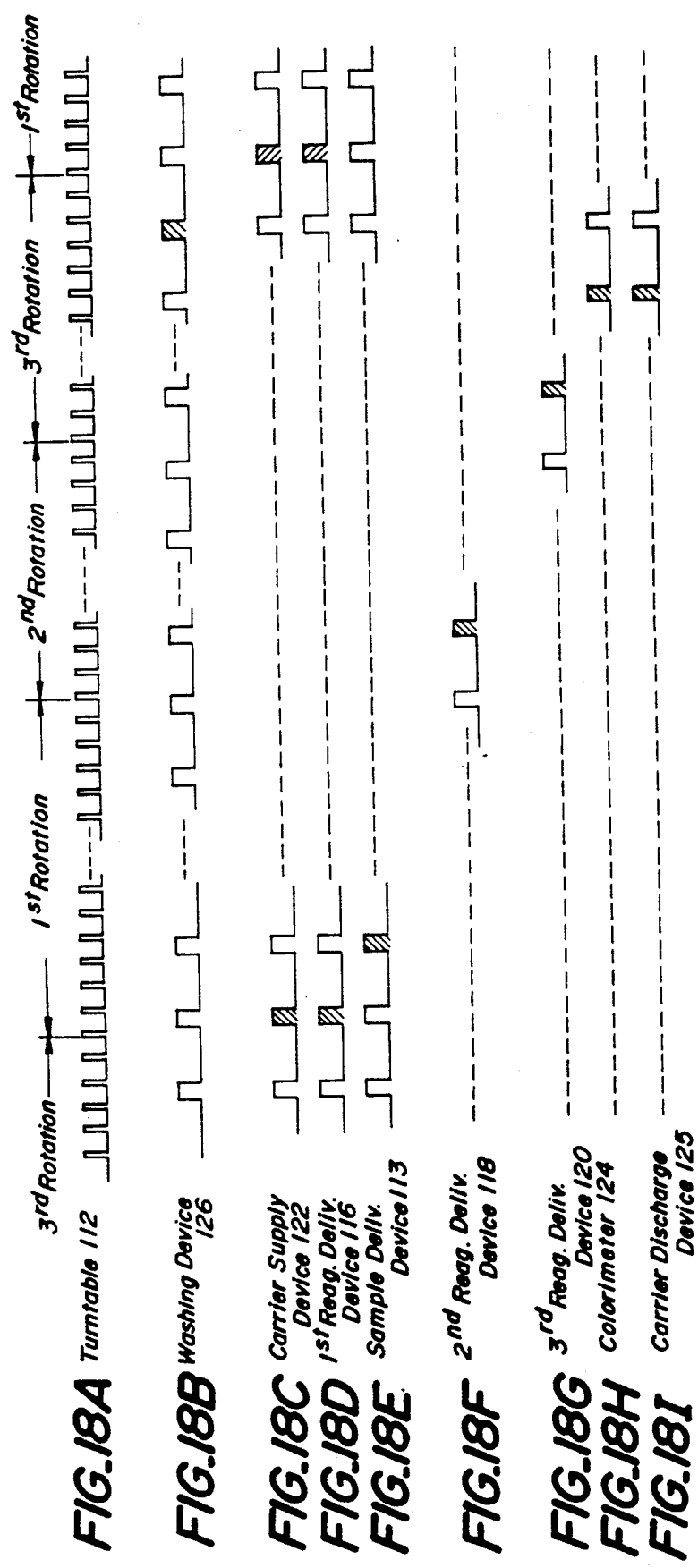
FIGS. 18A to 18I are timing charts for explaining an operation of the automatic analyzer shown in FIG. 17.

FIG. 17 is a schematic view showing another embodiment of the automatic enzyme-immuno-assay analyzer according to the invention, which utilizes the sandwich method. Portions in FIG. 17 similar to those shown in FIG. 12 are denoted by the same reference numerals used in FIG. 12. In this embodiment, since, it is necessary to effect the washing operation three times during the course of the analysis in case of using repeatedly the U-shaped tube, twenty five U-shaped tubes 111 are arranged on the turntable 112. The different point between this embodiment and that shown in FIG. 12 is that the washing operations are effected simultaneously for the three U-shaped tubes 111 positioned at the stop positions $S_{23}$ to $S_{25}$ by means of the washing device 126. In this case, it is not necessary to operate the washing device 126 every one pitch, but to operate it every three pitches the same as with the other devices. Therefore, the driving control is commonly used for all the devices. Moreover, in order to achieve such a construction, the carrier discharge device 125 is arranged at the stop position $S_{20}$.

FIGS. 18A to 18I are timing charts showing the operations of the analyzer shown in FIG. 17. As mentioned above, since the operations are almost similar to those shown in FIG. 12 and the different point is that the washing operations are effected every three pitches, the explanation of these timing charts are omitted here. As clearly understood from the timing charts shown in FIGS. 18A to 18I, even in this embodiment, it is possible to deliver the samples successively every three pitches.

Figure 19:
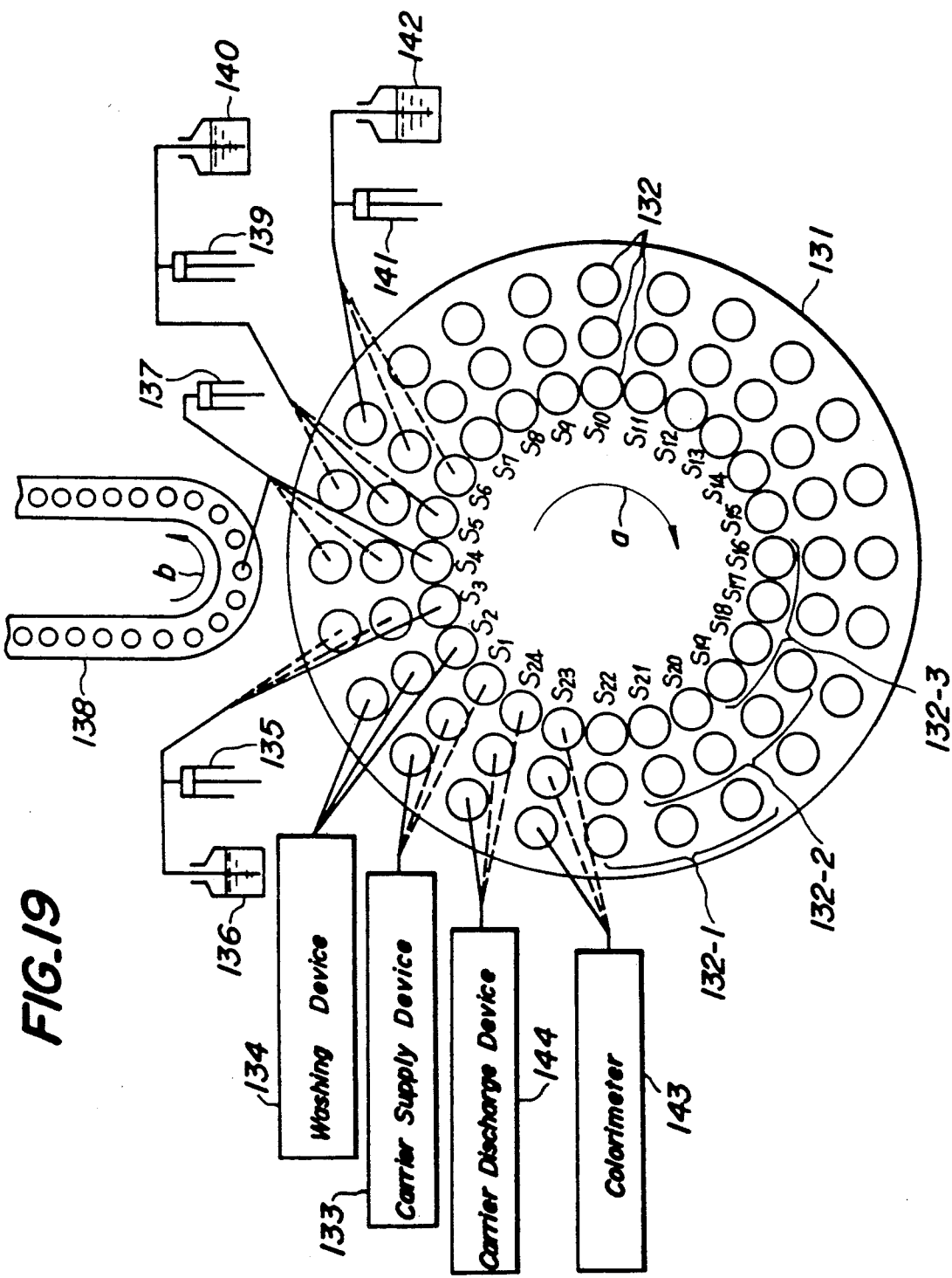
FIG. 19 is a schematic view depicting still another embodiment of the enzyme-immuno-assay automatic analyzer according to the invention.

FIG. 19 is a schematic view showing another embodiment of the automatic enzyme-immuno-assay analyzer according to the invention, which utilizes the sandwich method. In the embodiments explained heretofore, one concentric reaction line of the U-shaped tubes 111 is arranged on the turntable 112, but in this embodiment shown in FIG. 19, three concentric reaction lines of reaction tubes 132 each consisting of a test tube are arranged on a turntable 131. In this embodiment, each reaction line has twenty four reaction tubes 132, but this number of reaction tubes 132 can be arbitrarily determined. For the sake of simplicity, outermost, intermediate and innermost reaction lines are denoted respectively as a first reaction line 132-1, a second reaction line 132-2 and a third reaction line 132-3. As with the embodiments mentioned above, the turntable 131 is rotated intermittently at a predetermined pitch. A carrier supply device 133 is arranged at a stop position $S_1$ to supply the carrier selectively into the reaction tube 132. Moreover, the carrier supply device 133 functions to supply the carrier successively into the reaction tubes 132 located in the first, second and third reaction lines. That is to say, at first the carriers are supplied into all the successive reaction tubes 132 arranged in the first reaction line 132-1 one by one, and then the carriers are supplied into all the successive reaction tubes 132 arranged in the second reaction line 132-2 and are finally supplied into all the reaction tubes in the third reaction line 132-3. After that, this carrier supply operation is effected repeatedly.

Further, a washing device 134 is arranged at a stop position $S_2$ to wash simultaneously all the reaction tubes 132 located at this stop position $S_2$. A first reagent delivery device 135 is arranged at a stop position $S_3$ to deliver a first reagent 136 consisting of a buffer solution into the reaction tube 132. As with the carrier supply operation mentioned above, the first reagent 136 is delivered into all the reaction tubes arranged in the first, second and third reaction lines, respectively in this order. A sample supply device 137 is arranged at a stop position $S_4$ to deliver a sample supplied successively from a sample 138 into the reaction tube 132. Also this sample delivery operation is performed for the first, second and third reaction lines successively in this order. A second reagent delivery device 139 is arranged at a stop position $S_5$ to deliver a second reagent 140 consisting of the enzyme-labeled reagent into the reaction tube 132. A third reagent delivery device 141 is arranged at a stop position $S_6$ to deliver a third reagent 142 consisting of the color reagent into the reaction tube 132. Also these second and third reagent delivery operations are performed for the first, second and third reaction lines successively in this order.

Moreover, a colorimeter 143 is arranged at a stop position $S_{23}$ to effect the colorimetry of the test liquid contained in the reaction tube 132 after introducing the test liquid into the colorimetry flow cell. Further, a carrier discharge device 144 is arranged at a stop position $S_{24}$ to discharge the carrier remaining in the reaction tube. Also these colorimetry and carrier discharge operations are performed for the first, second and third reaction lines successively in this order.

FIGS. 20A to 20I are timing charts for explaining the operations of the analyzer shown in FIG. 19, and marks ①, ②, ③ denote the operations for the first, second and third reaction lines 132-1, 132-2 and 132-3, respectively. As shown in FIG. 20B, only the washing operation is performed simultaneously for the first, second and third reaction lines in synchronism with the rotation of the turntable 131.

First of all, at the stop position $S_1$ the one carrier is supplied into the reaction tube 132 arranged in the first reaction line 132-1 as shown in FIG. 20C. At the next stop position $S_2$, this reaction tube 132 is washed as shown in FIG. 20B. Since the prior test liquid is caused to remain in the reaction tube before the washing operation but this test liquid does not include the substance which will be coupled with the antibody or antigen on the carrier, the analysis is not affected by a contamination therebetween. Further, by washing the U-shaped tube at the stop position $S_2$, it is also possible to eliminate contaminations between the previous test liquid and the sample and between the previous test liquid and the reagent. At the next stop position $S_3$, a predetermined amount of the first reagent 136 consisting of the buffer solution is delivered into the reaction tube by means of the first reagent delivery device 135 as shown in FIG. 20D. Then at the stop position $S_4$, a predetermined amount of the sample is delivered into the reaction tube by means of the sample delivery device 137 as shown in FIG. 20E to start the first reaction. In this embodiment, these carrier supply, washing, first reagent delivery, sample delivery operations for the successive reaction tubes arranged in the first reaction line are performed every one pitch.

When the first reaction tube in the first reaction line into which the first sample is delivered reaches again the stop position $S_2$, the first B-F separation is effected by means of the washing device 134 as shown in FIG. 20B. In the course of this rotation, the relevant reaction vessel passes through the stop positions $S_5$, $S_6$, $S_{23}$ and $S_1$. However, as clearly seen from FIGS. 20A to 20I, at these stop positions the operations are performed for the reaction tubes arranged in the second and third reaction lines and thus these operations have no objection to the reaction tube in the first reaction line. Then, when the reaction tube reaches the stop position $S_5$, a predetermined amount of the second reagent 140 is delivered into the reaction tube by means of the second reagent delivery device 139 as shown in FIG. 20F to start the second reaction. Then, at the stop position $S_2$, the reaction tube is again washed as shown in FIG. 20B to effect the second B-F separation. After that, at the stop position $S_6$ a predetermined amount of the third reagent 142 is delivered into the reaction tube by means of the third reagent delivery device 141 as shown in FIG. 20G to start the third reaction. When the reaction tube reaches the stop position $S_{23}$, the colorimetry is performed by means of the colorimeter as shown in FIG. 20H. At the next stop position $S_{24}$, the carrier remaining in the reaction tube is discharged from the reaction tube by means of the carrier discharge device 144 as shown in FIG. 20I. Until this point, the reaction tube has been rotated three times and the analysis for one sample has been finished. In this embodiment, the operations mentioned above are effected repeatedly.

In this embodiment, by operating the carrier supply device 133, at first during the first rotation the carriers are supplied one by one into all the twenty four reaction tubes arranged in the first reaction line 132-1 successively, then during the second rotation the carriers are supplied one by one into all the twenty four reaction tubes arranged in the second reaction line 132-2, and finally during the third rotation the carriers are supplied into all the twenty four reaction tubes in the third reaction line 132-3. The operations mentioned above are repeatedly effected by the carrier supply device 133. As with the operations mentioned above, the operations of the sample delivery device 137, the first reagent delivery device 135, the second reagent delivery device 139, the third reagent delivery device 141, the colorimeter 143 and the carrier discharge device 144 are effected repeatedly, but the reaction line for which each operations is effected is different, as clearly understood from FIGS. 20A to 20I. For example, during the first rotation, the carrier supply operation is effected to the first reaction line 132-1, while the first reagent delivery operation is effected to the first reaction line 132-1 from the third pitch, the second reagent delivery operation is effected to the second reaction line 132-2 till the fourth pitch and to the third reaction line 132-3 from the fifth pitch, and the third reagent delivery operation is effected to the first reaction line 132-1 till the fifth pitch and to the second reaction line 132-2 from the sixth pitch. In this manner, according to the present embodiment, since the sample delivery operation can be effected every one pitch, it is possible to make the sample processing efficiency high as compared with the embodiments mentioned previously. Moreover, since the carrier supply and discharge, sample delivery, reagent delivery and colorimetry operations are performed successively for each of the reaction lines, the control of these operations can be made extremely easy.

In the embodiments of the automatic analyzer so far explained, use is made of carriers having given antigen or antibody fixed thereto. Thus there must be arranged the device for supplying the carriers into the reaction vessels one by one and the device for removing the carriers from the reaction vessels. Further, since the antibody or antigen is fixed to the carriers having a limited area, an amount of the antigen or antibody fixed to the carrier is also limited. Sometimes, it results in a decrease in the analysis accuracy.

According to the invention, the above mentioned drawbacks can be avoided by using reaction vessels on an inner wall of which has been fixed given antigen or antibody. Now, several embodiments of the automatic analyzer using such reaction vessels will be explained.

FIG. 21 is a schematic view illustrating an embodiment of the automatic analyzer according to the invention, in which the enzyme-immuno-assay is carried out by the sandwich method. The analyzer comprises a turntable 211 having thirty seven cuvette holders 213 in which cuvettes 212 can be detachably secured. On at least a part of the inner wall of the cuvette 212 is fixed given antibody or antigen. The turntable 211 is rotated in a direction a in a stepwise manner at a given pitch of, for example 15 seconds. Positions at which the cuvette holders 213 are stopped are denoted as $S_1$ to $S_{37}$. In the present embodiment, at a position $S_1$, cuvettes 212 are successively supplied into successive cuvette holders 213 of the turntable 211 by means of a cuvette supply device, i.e. a cuvette loading device 215. At a next position $S_2$, the cuvette is detected by a detector not shown and when the cuvette held in the cuvette holder 213 is detected, the cuvette 212 is washed with a washing liquid by means of a washing device 216 to effect the washing and B-F separation.

At the stop position $S_4$, a first reagent 218 is delivered by a first reagent delivery device 217, at a position $S_5$ a third reagent 220 is delivered by a third reagent delivery device 219, at a position $S_6$ a second reagent 229 is delivered by a second reagent delivery device 221, at a position $S_7$, a sample is delivered by a sample delivery device 223 from a sample cup 225 situating at a sample sucking position in a sampler 224, and at a position $S_{29}$ a fourth reagent 227 is delivered by a fourth reagent delivery device 226. As the first, second, third and fourth reagents 218, 229, 220 and 227, use is made of a buffer solution, an enzyme-labeled reagent, a color reagent, i.e. enzyme substrate, and a reaction stop reagent for stopping the reaction between the enzyme-labeled reagent and color reagent. In the present embodiment, the sampler 224 holds a number of racks 224a each supporting ten sample cups 225. The racks in a left column are successively moved downward in FIG. 21 and are then shifted leftward as shown by an arrow S into the sample sucking position. After all the ten samples in a rack have been delivered into cuvettes 212, the rack 224a is moved rightward into a lower end of a right rack column. Then the right column of racks is moved upward. In this manner a large number of samples in the sampler 224 can be successively indexed at the sample sucking position.

At a stop position $S_{32}$, a test liquid contained in the cuvette 212 is measured by a colorimeter 228. After that, at a position $S_{35}$ the cuvette 212 is removed from the turntable 211 by means of a cuvette discharge device 222. In the present embodiment, the test liquid is subjected to the direct photometry, while the test liquid is caused to remain in the cuvette and then the cuvette 212 and the test liquid are separately collected into a waste cuvette container and a waste liquid container, respectively.

Now the operation of the analyzer shown in FIG. 21 will be described also with reference to FIGS. 22A to 22C and 23A to 23J.

In the present embodiment, respective samples are analyzed by the sandwich method during a period in which the turntable 211 is rotated by about three revolutions. Therefore, the delivery of the first to fourth reagents, the supply and discharge of cuvettes and the colorimetry are effected once each time the turntable 211 is rotated by three pitches. However, since the washing is effected by three times for respective cuvettes 212, the washing device 216 is operated each time the turntable 211 is rotated by one pitch. To this end, at the position $S_2$ there is provided the detector for detecting the existence or non-existence of the cuvette. Further, in order to operate the analyzer in this manner, the number of cuvettes 212 held in the cuvette holders 213 must be set to $3n+1$ or $3n+2$, wherein n is a positive regular number 1, 2, 3 . . . . In the present embodiment, $n=12$ and there are provided thirty seven cuvette holders 213.

Figure 22A:
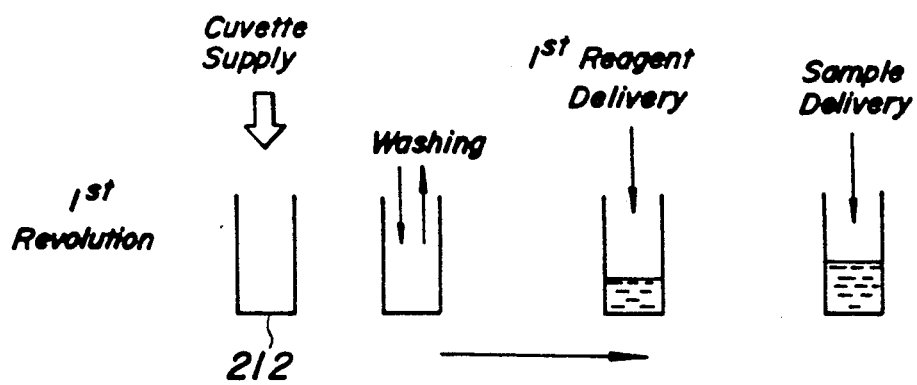
FIGS. 22A to 22C are schematic views illustrating an operation of the automatic analyzer shown in FIG. 21.
Figure 22B:
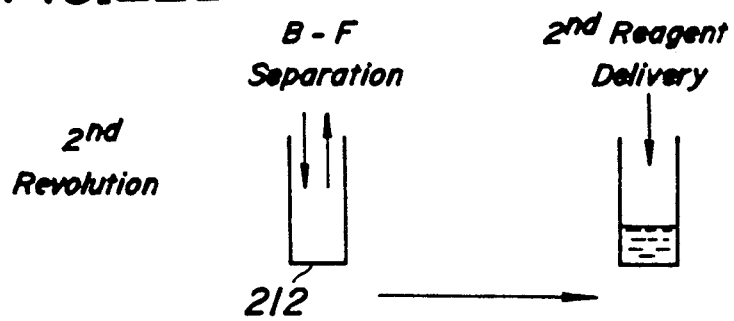
Figure 22C:
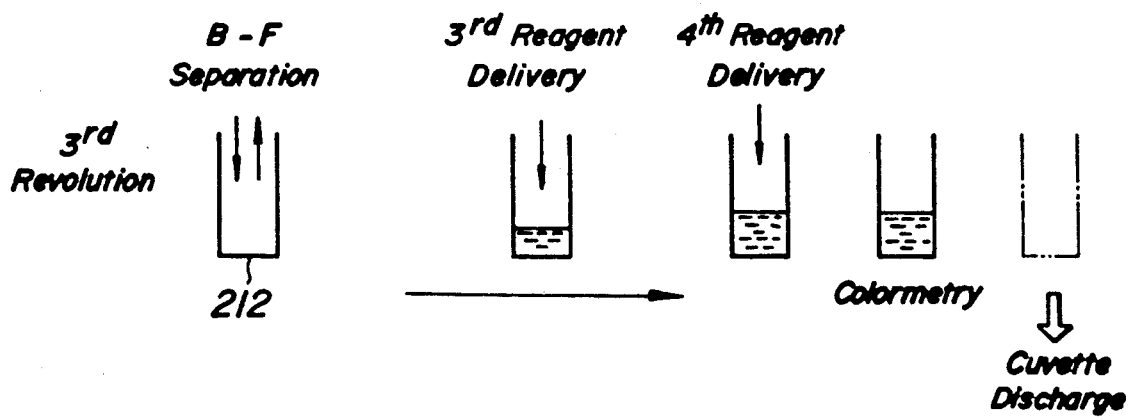

During a first revolution of the turntable 211, at the position $S_1$, a cuvette 212 is supplied into a cuvette holder 213 by the cuvette supply device 215 as shown in FIG. 22A. On the inner wall of the cuvette there has been previously fixed given antibody or antigen. At the position $S_2$, the cuvette 212 is washed by the washing device 216. At the position $S_4$ which is downstream with respect to the position $S_1$ by three pitches, a given amount of the first reagent 218, i.e. the buffer solution, is poured into the cuvette 212 by the first reagent delivery device 217 to start the first antigen-antibody reaction. In FIGS. 23B to 23J various operations effected for the relevant cuvette are denoted by hatching.

During a second revolution of the turntable 211, at the position $S_2$ the first B-F separation is performed by the washing device 216. Then, at the position $S_6$ a given amount of the second reagent 229, i.e. the enzyme-labeled reagent, is delivered into the cuvette 212 by means of the second reagent delivery device 221 to initiate the second antigen-antibody reaction.

During a third revolution of the turntable 211, at the position $S_2$ the second B-F separation is carried out by the washing device 216. Next at the position $S_5$ a given amount of the third reagent 220, i.e. the color reagent containing the enzyme substrate, is delivered into the cuvette 212 to start the color reaction. Then, at the position $S'_{22}$ a given amount of the reaction stop reagent 227 is poured into the cuvette by the fourth reagent delivery device 226. At the position $S_{32}$, the test liquid formed in the relevant cuvette 212 is directly measured by the colorimeter 228 via the cuvette. At the position $S_{35}$, the cuvette 212 is discharged from the turntable 211 by the cuvette discharge device 229. After the turntable 211 has been rotated by three pitches, a new cuvette is delivered into the relevant cuvette holder by the cuvette supply device 215. In FIGS. 23A to 23E, the operations for this newly supplied cuvette are denoted by cross hatching.

As explained above, the analysis for a single sample is carried out for a time period during which the turntable 211 is rotated by substantially three revolutions. In the present embodiment, the sample delivery, the first to fourth reagent deliveries, the cuvette supply and discharge and colorimetry are effected every time the turntable 211 is moved by three pitches and further the number of cuvettes held in the turntable is set to $3 \times 12 + 1 = 37$. Therefore, cuvettes which are successively indexed at, for instance the position $S_7$ deviate one by one every time the turntable is rotated by one revolution. This is the case for all the operations which are effected once every time the turntable is rotated by three pitches. Therefore, the sample delivery can be performed regularly once for every three pitches and thus, the ID control for samples and the treatment of analytic data can be effected at a constant period. In this manner, various kinds of control can be carried out simply. Also in this embodiment, a plurality of washings including the B-F separation can be performed by passing the cuvette repeatedly through the single washing device and therefore, the analyzer can be made small in size and simple in construction. Moreover, since the cuvette is used as the carrier for fixing given antigen or antibody, it is not necessary to use the separate carriers in the previous embodiments and thus, the running cost can be decreased.

Figure 24:
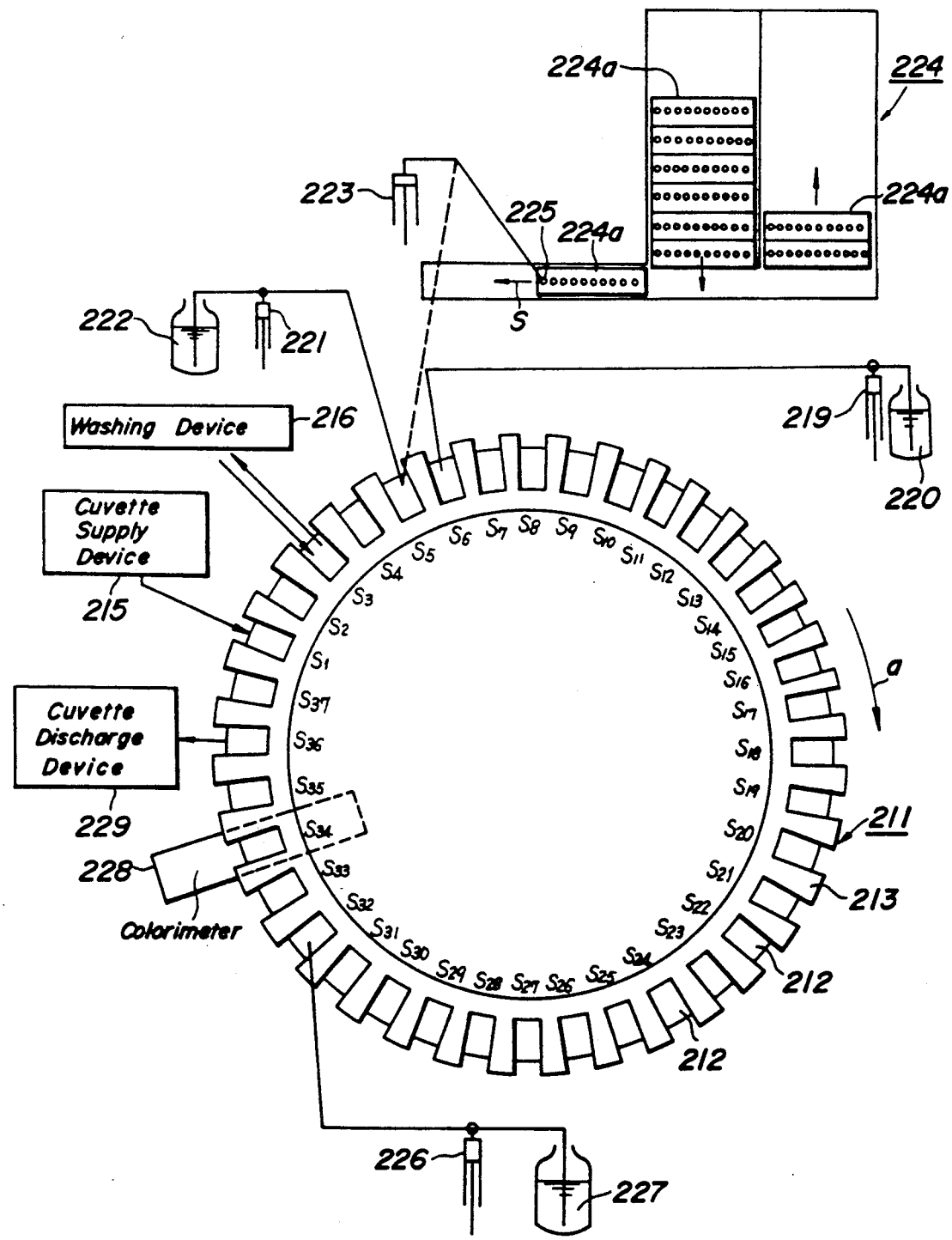
FIG. 24 is a schematic view depicting still another embodiment of the enzyme-immuno-assay automatic analyzer according to the invention.

FIG. 24 is a schematic view illustrating another embodiment of the automatic analyzer according to the invention, in which the enzyme-immuno-assay is performed in competitive method by using the cuvettes having given antibody or antigen fixed on inner walls thereof. In the present embodiment, portions similar to those of the embodiment shown in FIG. 21 are denoted by the same reference numerals used in FIG. 21. In the competitive method, the washing is effected twice and thus, $2n+1$ cuvette holders 213 are provided in the turntable 211. Then, the sample delivery, reagent delivery, supply and discharge of cuvette and colorimetry are performed once every time the turntable is rotated by two pitches. At a position $S_3$, the cuvette is detected by a detector (not shown) and the washing is effected by the washing device 216. At a position $S_5$, a given amount of a first reagent, 222, i.e. the enzyme-labeled reagent is poured into the cuvette by the first reagent delivery device 221 and at the same time a given amount of a sample is poured by the sample delivery device 223. Also in the present embodiment, successive samples contained in sample cups 225 are indexed into the sample sucking position by means of the sampler 224 comprising a number of sample cup racks 224a. At a position $S_6$, a given amount of a second reagent 220, i.e. the color reagent, is delivered into the cuvette by the second reagent delivery device 219. At a position $S_{32}$, a given amount of a third reagent 227, i.e. the reaction stop reagent, is poured by the third reagent delivery device 226. Further, at a position $S_{34}$, the test liquid contained in the cuvette is measured by a colorimeter 228 via the cuvette and at a position $S_{36}$, the waste cuvette 212 is removed from the cuvette holder 213 by the cuvette discharge device 229 and the vacant cuvette and test liquid are contained in separate containers.

FIGS. 25A to 25I show timing charts of various operations of the analyzer illustrated in FIG. 24. At the position $S_1$, a cuvette 212 is supplied into a cuvette holder 213 of the turntable 211. After the rotation of the turntable by two pitches, at the position $S_3$ the cuvette is washed by the washing device 216. After further two pitches, at the position $S_5$ the enzyme-labeled reagent 222 and sample are delivered into the cuvette 212 to initiate the antigen-antibody reaction. During the second revolution of the turntable 211, the B-F separation is effected at the position $S_3$ by the washing device 216. Then, the color reagent 220 is poured into the cuvette 212 by the delivery device 219 to initiate the color reaction. This reaction is finished when the reaction stop reagent 227 is supplied into the cuvette by means of the delivery device 226. Next, at the position $S_{34}$, the test liquid is measured by the colorimeter 228 via the cuvette 212. Finally, at the position $S_{36}$, the cuvette is removed from the turntable 211 by the cuvette discharge device 229. In FIGS. 25B to 25I, the operations relating to the relevant sample are denoted by hatching and operations for a next sample are represented by cross hatching. In this manner, the analysis for respective samples can be performed every time the turntable is rotated by two revolutions. Further, the various operations such as the sample delivery, reagent deliveries, supply and discharge of cuvette and colorimetry are performed once each time the turntable is rotated by two pitches and thus, the control of the analyzer can be effected in a simple manner. It should be noted that the washing operation by the washing device 216 has to be performed every time the turntable 211 is rotated by one pitch.

Now concrete constructions of the various portions of the automatic analyzers shown in FIGS. 21 and 24 will be explained.

Figure 26A:
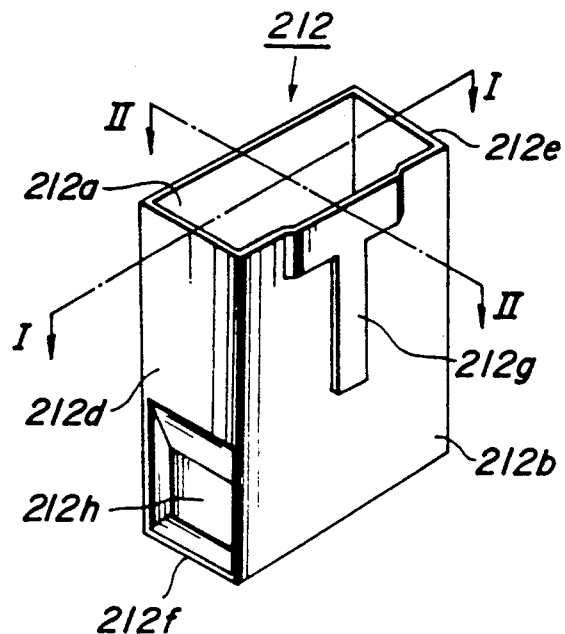
FIGS. 26A to 26C are perspective and cross sectional views showing an embodiment of the cuvette according to the invention.
Figure 26B:
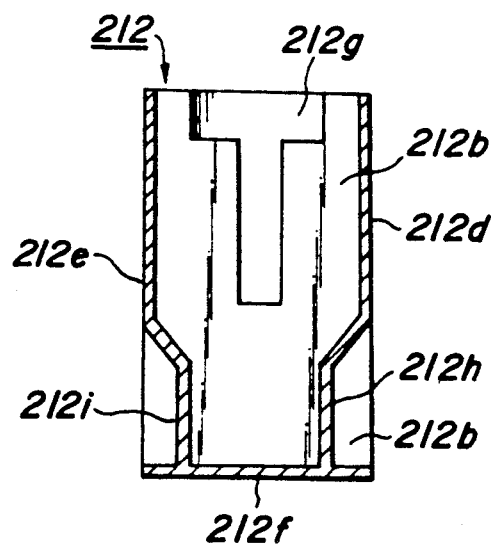
Figure 26C:
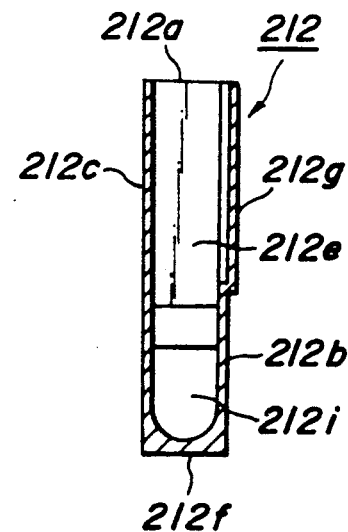

FIG. 26A is a perspective view showing an embodiment of the cuvette type reaction vessel according to the invention and FIGS. 26B and 26C are cross sections cut along lines I—I and II—II in FIG. 26A, respectively. In the present embodiment, the cuvette 212 is formed by a mold of transparent synthetic resin and has generally a flat box shape. The cuvette 212 has an opening 212a at its top, two main walls 212b and 212c, two side walls 212d and 212e and a bottom wall 212f. Onto at least a part of the inner wall of the cuvette is fixed given antibody or antigen which selectively reacts with substance to be analyzed. In one of the main walls 212b there is formed a T-shaped projection 212g which serves to hold the cuvette in a cuvette holder due to its elastic force as will be explained later. The side walls 212d and 212e of the cuvette are arranged perpendicularly to a measuring optical axis and include entrance and exit windows 212h and 212i for a measuring light beam. As best shown in FIG. 26B, the windows 212h and 212i are retarded inwardly with respect to the side walls 212d and 212e, respectively and side edges of the main walls. That is to say, the measuring windows 212h and 212i are surrounded by the main walls 212b and 212c and the bottom wall 212f and therefore, the windows are effectively protected against stain and injury, which ensures a high measuring accuracy. Further, an inner surface of the bottom wall 212f is formed semi-cylindrically. This results in that the photometry can be carried out for a very small amount of the test liquid.

The antibody or antigen can be fixed to the inner surface of the cuvette made of plastics by means of the known physical absorption method or chemical binding method. Further, if the existence of proteins such antigen, antibody and labeling enzyme might influence the photometry, the windows 212h and 212i are kept free from the antibody or antigen.

Figure 27:
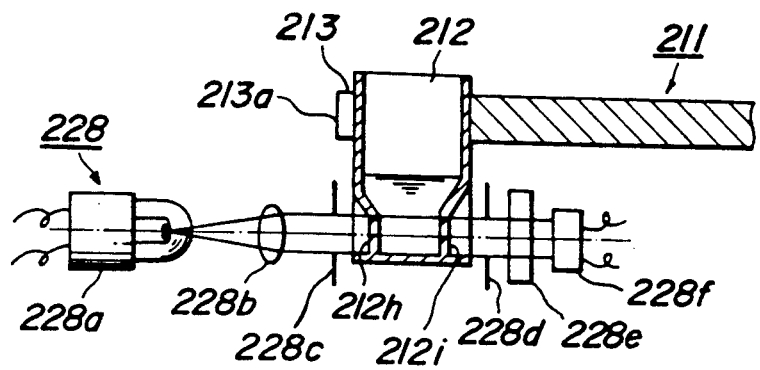
FIG. 27 is a schematic cross section illustrating a photometering device using the cuvette according to the invention.

FIG. 27 shows an embodiment of a photometering station in which an absorbance of the test liquid contained in the cuvette 212 is measured. A light beam emitted from a lamp 228a is collimated by a lens 228b and is made incident upon the entrance window 212h of the cuvette 212 via a stop 228c. A light flux emanating from the exit window 212i is made incident upon a light detector 228f by means of a stop 228d and an optical filter 228e. The cuvette 212 is held in a recess 213a of the cuvette holder 213 formed in the turntable 211 at its periphery due to the elasticity of the cuvette.

Figure 28:
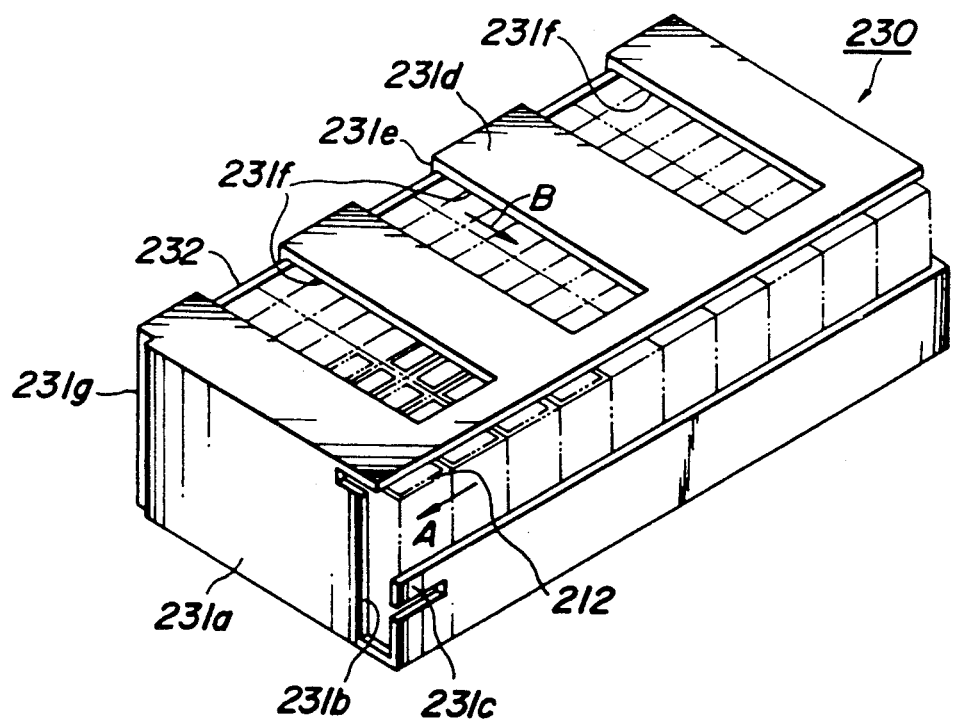
FIG. 28 is a perspective view illustrating an embodiment of a cuvette magazine according to the invention.

A large number of cuvettes 212 are arranged in a magazine 230 as illustrated in FIG. 28. It is not necessary at all for an operator of the analyzer to insert the cuvettes in the magazine, but the magazine having the cuvettes previously contained therein is available. Therefore, the cuvettes can be further protected against the stain and injury. The magazine 230 may be formed by a mold of plastics or metal. In the present embodiment, the magazine has such a length viewed in a direction A that ten cuvettes are arranged side by side and such a width measured in a direction B that also ten cuvettes are arranged side by side. Therefore, the magazine can contain a hundred cuvettes in a matrix form. In a side wall 231a of the magazine 230 is formed an outlet 231b having a width which is substantially equal to the width of the cuvette 212 and a height which is nearly equal to the height of the cuvette 212. In order to ensure that the cuvette 212 can be discharged out of the magazine 230 through the outlet 231b in a correct posture, a resilient strip 231c is formed in a front wall of the magazine at a portion adjacent to the outlet 231b by providing a recess in the wall. In top walls 231d and bottom walls of the magazine are formed three recesses 231f. It should be noted that the recesses 231f do not extend in the upper wall 231d up to the front edge so that the cuvettes in a first column are not situated under the recesses. This ensures smooth movement of the cuvettes. In the magazine there is inserted a push plate 232 between the assembly of the cuvettes and the rear wall 231e. As will be explained hereinafter, the cuvette array may be moved in the direction B by moving the plate 232 in this direction B. Along a right hand side edge of the side wall 231a is formed a step 231g which avoids an inverse insertion of the magazine into an automatic cuvette loader having a corresponding projection.

Figure 29:
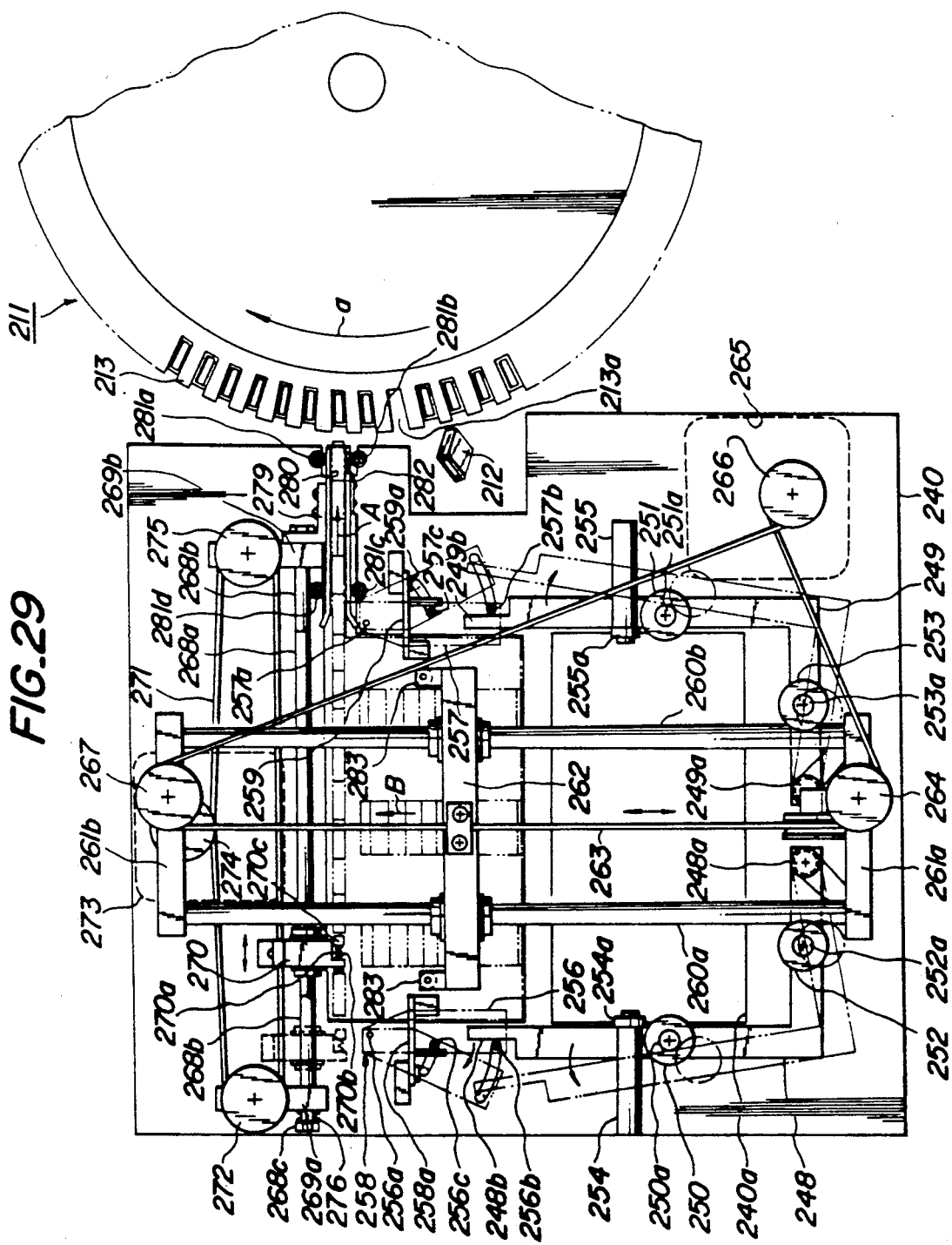
FIG. 29 is a plan view depicting an embodiment of an automatic cuvette loading apparatus according to the invention.
Figure 30:
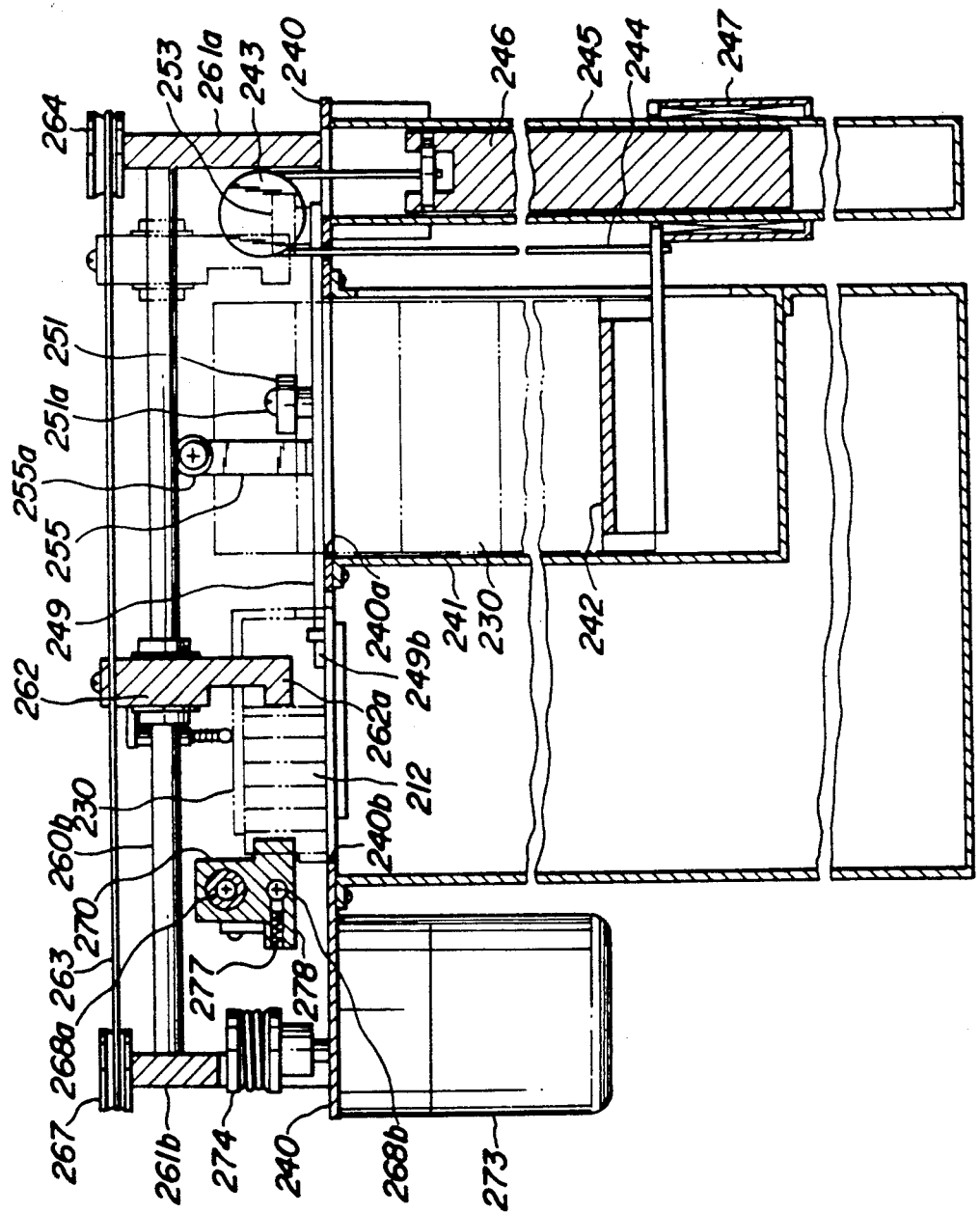
FIG. 30 is a cross sectional view showing the apparatus shown in FIG. 29.

FIGS. 29 and 30 illustrate an embodiment of the automatic cuvette loader according to the invention for supplying the cuvettes 212 in the magazine 230 one by one into successive recesses 213a of the cuvette holder 213 of the turntable 211. The turntable 211 is rotated in a direction a in FIG. 29 in a stepwise manner at the given pitch to form a circular reaction line.

The cuvette auto-loader supply device, i.e. a cuvette supply device, comprises a base plate 240, and to a rear surface of the base plate 240 is secured a magazine container 241 as best shown in FIG. 30. In the magazine container 241 is arranged movably up and down a magazine support 242 to which is secured one end of a wire 244 whose other end is connected via a pulley 243 to a weight 246 which is movably supported in a cylindrical guide 245. Therefore, the magazine support 242 is biased upwardly. In the magazine container 241 there may be arranged a plurality of the magazines 230 each containing a hundred cuvettes 212. Pusher 283 is urged against the upper surface of magazine 230 as shown and coil spring 284 biases pusher 283 against magazine 230.

In the base plate 240 is formed a first opening 240a above the magazine container 241 and the opening 240a has such a dimension that the magazine 230 can pass therethrough. On the upper surface of the base plate 240 are arranged L-shaped levers 248 and 249 rotatable about shafts 248a and 249a, respectively. To these levers are secured ring-shaped stoppers 250 and 251 by means of shafts 250a and 251a, respectively. As explained later, to the levers 248 and 249 are also secured rollers 252 and 253 by means of shafts 252a and 253a. In free ends of the L-shaped levers 248 and 249 are further formed projections 248b and 249b, respectively. Besides the opening 240a of the base plate 240 there are further arranged L-shaped posts 254 and 255 and stoppers 254a and 255a are secured to the posts.

In the base plate 240 there is further formed a second opening 240b through which the magazine can be passed. Beside the second opening 240b a pair of magazine support levers 256 and 257 are arranged rotatably about shafts 256a and 257a. Near free ends of these levers are secured pins 256b and 257b, respectively, these pins being engaged with the projections 248b and 249b of the levers 248 and 249, respectively. To the levers 256 and 257 are further secured pins 256c and 257c which are engaged with projections of push levers 258 and 259 which are arranged rotatably about shafts 258a and 259a, respectively extending in parallel with the plane of the drawing of FIG. 29. The levers 248, 249, 256, 257, 258 and 259 are biased by means of springs not shown into positions shown by solid lines. When the levers 256 and 257 are moved as depicted by imaginary lines, the push levers 258 and 259 are rotated in a plane perpendicular to the plane of the drawing of FIG. 29.

To the base plate 240 are further secured two guide shafts 260a and 260b by means of leg portions 261a and 261b, the guide shafts extending above the first and second openings 240a and 240b. A first slider 262 is movably secured to the guide shafts 260a and 260b by means of linear bearings. To the first slider 262 is secured a wire 263 which is wound around a pulley 264 provided on the leg portion 261a, a pulley 266 secured to a driving shaft of a motor 265 and a pulley 267 provided on the leg portion 261b. When the motor 265 is driven in both directions, it is possible to move the first slider 262 in a direction B along the guide shafts 260a and 260b in a reciprocal manner. By this movement, it is possible to transfer the magazine 230 situated above the first opening 240a into a cuvette charging position above the second opening 240b and to feed the cuvettes 212 in the magazine 230 in the direction B. For this purpose, to the lower surface of slider 262 are secured three arms 262a which can be inserted in the recesses 231f formed in the magazine 230 and are made in contact with the push plate 232.

There are further provided a pair of guide shafts 268a and 268b extending perpendicularly to the guide shafts 260a and 260b, the guide shafts 268a and 268b being coupled with the base plate 240 by means of leg portions 269a and 269b. To these guide shafts 268a and 268b is slidably mounted a second slider 270 to which is connected a wire 271 extending around a pulley 272 secured to the leg portion 269a, a pulley 274 connected to a driving shaft of a motor 273 and a pulley 274 connected to a driving shaft of a motor 273 and a pulley 275 secured to the leg portion 269b. When the motor 273 is driven in both directions, the second slider 270 can be moved reciprocally in the direction A along the guide shafts 268a and 268b. By this movement, the cuvettes 212 in the magazine 230 can be inserted into the recesses 213a of the cuvette holder 213 one by one. To this end, to the slider 270 is slidably secured a pin 270a to which a pushing claw 270c is connected and a coiled spring 270b is arranged around the pin 270a. Then, it is possible to push resiliently the cuvette 212 situated at an extreme position in the magazine 230 by means of the pushing claw 270c.

There is inserted a coiled spring 276 between the guide shaft 268b and the leg portion 269a and the guide shaft 268b is slidably mounted on the leg portion 269a and therefore, the guide shafts 268a and 268b are biased in the leftward direction in FIG. 29. Further, as shown in FIG. 30, the slider 270 is slidably secured to the guide shaft 268a by means of a linear bearing, but is coupled with the guide shaft in a frictional manner by means of a coiled spring 277 and a ball 278. Therefore, the slider 270 and guide shaft 268b can be moved together over a certain limited range. To the other end of guide shaft 268b is connected an L-shaped rail supporting member 279 to which is secured a guide rail 280 having a trough construction whose width is substantially equal to the width of the cuvette 212, The guide rail 280 is supported by guide rollers 281a, 281b, 281c and to 281d and can be moved in the direction A over a relatively small distance. Near a tip of the guide rail is arranged a leaf spring 282 for pressing the cuvette situated at the tip of guide rail 280.

Now the operation of the automatic cuvette loader of this embodiment will be explained. It is assumed that in the magazine container 241 there are set several magazines 230 and the uppermost magazine is engaged with the stoppers 250 and 251 secured to the levers 248 and 249, respectively, so that the magazine stock does not move upwardly furthermore. Above the second opening 240b is positioned a magazine 230 which is supported by the levers 256 and 257, so that it does not fall down in the opening 240b. The magazine situated at the cuvette charging position above the second opening 240b contains a number of cuvettes 212 to be successively supplied into the respective recesses 213a of the cuvette holder 213 of the turntable 211. When the motor 273 is driven in a forward direction, the wire 271 is rotated in the clockwise direction in FIG. 29 and thus, the slider 270 is moved in the direction A. At the same time, the guide shaft 268b is moved also in the direction A and thus, the rail supporting member 279 and guide rail 280 are also moved in the direction A. During this movement, the first cuvette column (the uppermost horizontally aligned cuvettes in FIG. 29) is moved also in the direction A. The guide shaft 268b is moved in the direction A until a nut 268c provided on the right hand end of guide shaft 268b is engaged with the leg portion 269a, and after that, only the slider 270 is further moved in the direction A. By this movement of the slider 270, the cuvette column is moved in the direction A and the left hand cuvette is discharged out of the guide rail 280 and is inserted into the recess 213a of the cuvette holder 213, which recess is just situated opposite to the guide rail 280. As explained above, the cuvette 212 has the T-shaped projection 212g formed in its main wall 212b and therefore, the cuvette 212 is resiliently clamped in the recess 212a. Next the motor 173 is driven in the reverse direction and the slider 270 and guide shaft 268b are moved in a direction opposite to the direction A until the rail supporting member 279 makes contact with the leg portion 269b. During this reverse movement, the pushing claw 270c of the slider 270 is always caused to make contact with the cuvette.

By repeating the above operation, successive cuvettes 212 in the uppermost column in FIG. 29 can be supplied into respective recesses 213a of the cuvette holder 213 one by one. After that the motor 273 is driven in the reverse direction and the slider 270 is returned into the right hand position in FIG. 29. Then, the motor 265 is driven in a forward direction by a predetermined amount and the wire 263 is rotated in the counter-clockwise direction in FIG. 29. During this movement, the first slider 262 is moved in the direction B by a distance equal to the width of the cuvette 212 and the cuvettes remaining in the magazine 230 are moved in the direction B by means of the pushing plate 232.

In this manner, all the cuvettes 212 in the magazine 230 can be successively supplied into the reaction line constituted by the cuvette holder 213 in the turntable 211. After that, the motor 265 is driven in a reverse direction and the slider 262 is moved in a direction opposite to the direction B into the lowermost position in FIG. 29. At the end of this movement of the slider 262, the slider 262 is engaged with the rollers 252 and 253 on the levers 248 and 249. Then the levers 248 and 249 are rotated into positions shown by chain lines and the ring-shaped stoppers 250 and 251 are disengaged from the magazine 230. Then the uppermost magazine in the magazine container 241 is moved above the base plate 240 via the first opening 240a and is engaged with the stoppers 254a and 255a. When the levers 248 and 249 are rotated, the arms 256 and 257 are also rotated by means of the engagement of the projections 248b and 249b with the pins 256b and 257b, into positions illustrated by chain lines, so that the empty magazine is fallen down through the second opening 240b. In order to enhance the operation for discharging the empty magazine from the cuvette loading position, the pushing levers 258 and 259 are rotated in conjunction with the rotation of the arms 256 and 257 so as to push the magazine downward.

Finally, the motor 265 is driven in the forward direction and the slider 262 is moved upward in FIG. 29 and the levers 248, 249, 256, 257, 258 and 259 are returned to the positions shown by solid lines. In this manner, the new magazine can be set into the cuvette loading position.

The present invention is not limited to the embodiments explained above, but may be modified in various manners. For instance, in the above embodiments a hundred cuvettes are contained in a single magazine, but any desired number of cuvettes may be contained in the magazine. Further, a single array of a plurality of cuvettes may be arranged in an elongated magazine. In such a case, it is not necessary to move the cuvettes in the direction B in the magazine. Moreover, in the above embodiment, the used cuvettes are wasted, but they may be used repeatedly after washing them.

It should be further noted that the construction of the cuvette is not limited to that shown in FIGS. 26A to 26C.

For instance, the T-shaped projection 212g may be formed in both the main walls 212b and 212c. Further, legs may be provided by extending the side walls 212d and 212e beyond the bottom wall 212f. In this case, the outer bottom surface may be also shaped circularly corresponding to the semi-cylindrical inner bottom surface.

According to the embodiment just explained above, the reaction cuvettes can be successively supplied into the reaction line in a positive and accurate manner without staining and injuring the cuvettes, so that the reliability and accuracy of measurement can be increased materially. Further, the automatic cuvette loader has a simple construction and can be made less expensive. Moreover, the entrance and exit windows of the cuvette are effectively protected by the surrounding walls against stain, injury and stray light, and the measuring precision can be made much higher. Further, a number of cuvettes are contained in the magazine and thus, and the transportation and management of the cuvettes can be easily effected without staining and injuring the cuvettes. Moreover, the cuvettes may be supplemented in a prompt manner during the analysis without interrupting the measurement.

Figure 31:
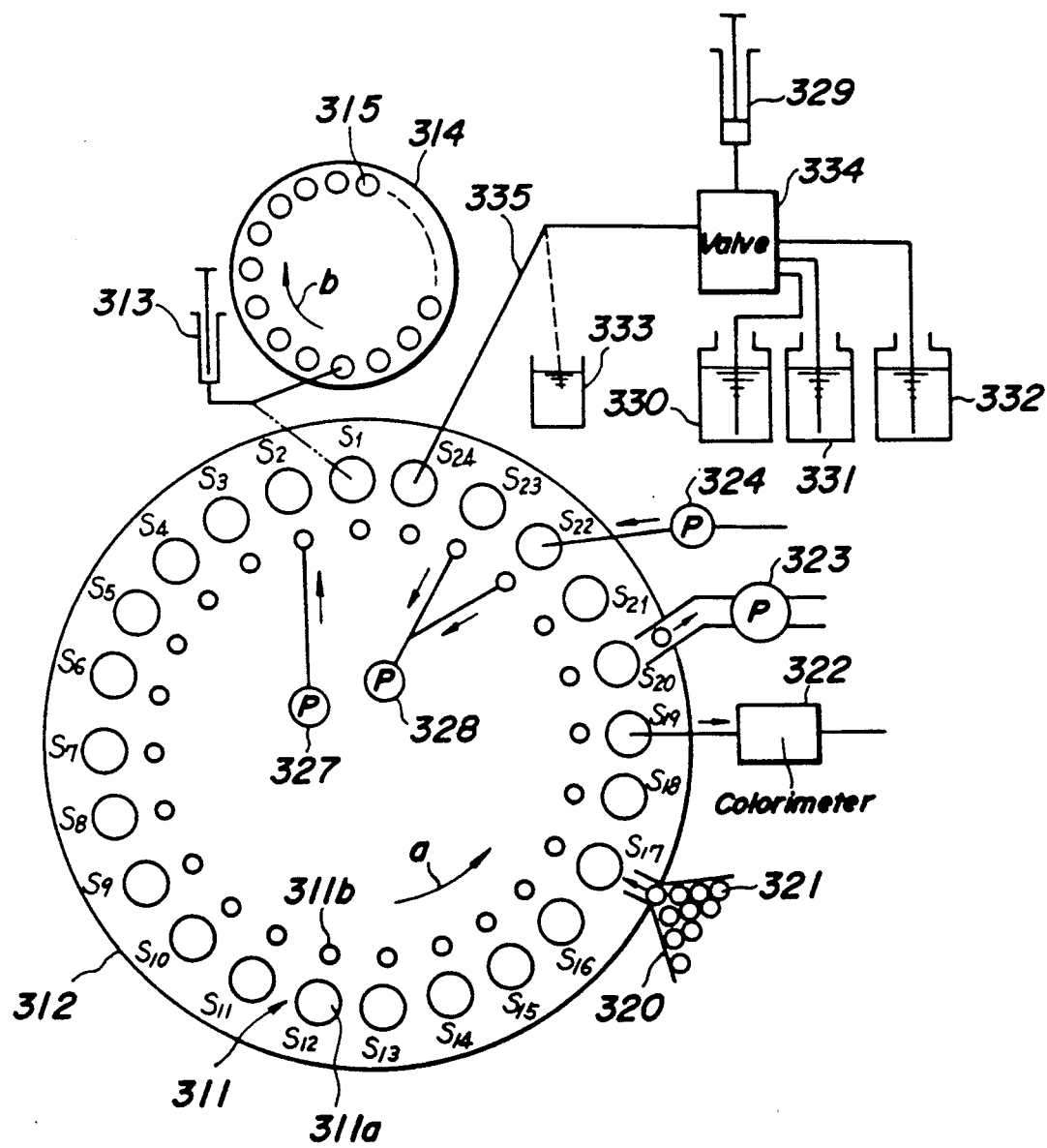
FIG. 31 is a schematic view illustrating still another embodiment of the enzyme-immuno-assay automatic analyzer according to the invention.

FIG. 31 is a schematic view showing another embodiment of the enzyme-immuno-assay automatic analyzer according to the invention which performs the sandwich method explained above with reference to FIG. 2. On a turntable 312 are arranged equidistantly twenty four U-shaped tubes 311 along a periphery of the turntable. The turntable 312 is intermittently rotated in a direction shown by an arrow a at a given period of, for example 15 seconds, while the U-shaped tubes 311 are dipped into a thermostat. Positions at which the U-shaped tubes 311 are stopped due to the stepwise rotation of the turntable 312 are denoted as $S_1$ to $S_{24}$. In the present embodiment, into a U-shaped tube 311 positioned at $S_1$ is delivered a sample from a sample cup 315 which is situated just at a sample sucking position of a sampler 314 by means of a sample delivery device 313. The sampler 314 holds twenty four sample cups 315 arranged equidistantly along a disc which is rotated intermittently in a direction b in synchronism with the rotation of the turntable 312. Into a U-shaped reaction tube 311 situated at $S_{17}$ is supplied a carrier 312 such as a synthetic resin particle or glass bead from a carrier supply device 320. It should be noted that the carrier 321 has a diameter smaller than an inner diameter of the large mouth portion 311a of the U-shaped tube 311, but is larger than an inner diameter of the small mouth portion 311b. On an outer surface of the carrier 321 there has been previously fixed antibody or antigen which causes the antigen-antibody reaction with antigen or antibody substance in the sample to be tested. Further, in the carrier supply device 320, the carriers 321 are wetted with a buffer solution. A reaction liquid in a U-shaped tube 311 at a position $S_{19}$ is selectively sucked into a colorimeter 322, and a carrier 321 contained in a U-shaped tube 311 at a position $S_{20}$ is removed therefrom by means of a carrier discharge device 323. Into a U-shaped tube 311 at a position $S_{22}$ is supplied a washing liquid such as ion exchange water, buffer solution for immunological analysis, physiological saline solution, etc. by means of a washing pump 324. At position $S_2$, a stirring air pump 327 can be detachably connected to small mouth portions 311b of U-shaped tubes 311, and at positions $S_{22}$ and $S_{23}$, a discharge pump 328 can be detachably connected to small mouth portions 311b of U-shaped tubes 311. In a U-shaped tube situating at a position at $S_{24}$ is selectively delivered one of a buffer solution 330, an enzyme-labeled reagent 331 and a color reagent 332 by means of a reagent delivery device 329 of a syringe type.

On end of a reaction tube is connected to the reagent delivery device 329, and the other end thereof is connected to a nozzle 335 which is transferred to a position $S_{24}$ or a washing liquid tank 333 by means of a transfer means not shown. Moreover, a valve 334 is arranged in a middle of the reagent tube, to which a buffer solution tank 330, an enzyme-labeled reagent tank 331 and a color reagent tank are connected through respective tubes. By changing the valve 334, the buffer solution, the enzyme-labeled reagent and the color reagent are selectively delivered into the U-shaped tube 311 positioned at the position $S_{24}$.

Now, the operation of the automatic analyzer shown in FIG. 31 will be explained.

During a first revolution of the turntable 312, at the position $S_{17}$, a carrier 321 wetted with the buffer solution is supplied in a U-shaped tube 311 via its large mouth portion 311a. Then, at the position $S_{22}$, the washing liquid is intermittently poured into the U-shaped tube 311 from the large mouth portion 311a by means of the washing pump 324 and at the same time, the washing liquid is sucked out of the tube 311 via the small mouth portion 311b by means of the discharge pump 328. Next, at the position $S_{23}$, any washing liquid remaining in the tube 311 is discharged by the discharge pump 328.

Then, at the position $S_{24}$ a given amount of the buffer solution is delivered into the U-shaped tube 311 via its large mouth portion 311a by means of the delivery device 329 after changing the valve 334 to select the buffer solution tank 330. Then, at the position $S_1$ a given amount of a sample is delivered by means of the sample delivery device 313 into the tube 311 from a sample cup 315 situated at the sample sucking position of the sampler 314. Next, at the position $S_2$, an air stream is supplied into the U-shaped tube 311 by means of the air pump 327 to stir the buffer solution and sample in the tube 311. In this manner, a first antigen-antibody reaction is initiated. It should be noted that the carrier supply device 320, buffer solution delivery device 325, sample delivery device 313 and sampler 314 are made inoperative after being once operated for respective U-shaped tubes.

During a second revolution of the turntable 312, at the position $S_{22}$, the liquid in the tube 311 is sucked via the small mouth portion 311b by the discharge pump 328 and at the same time, the washing liquid is intermittently poured into the tube via its large mouth portion 311a by means of the washing pump 324. The washing liquid remaining in the tube is discharged at the positions $S_{22}$ and $S_{23}$. In this manner, the U-shaped tube 311 and the carrier 321 contained therein are fully washed to effect a first B-F separation. Then, at the position $S_{24}$, a given amount of the emzyme-labeled reagent is delivered into the U-shaped tube 311 via its large mouth portion 311a by the reagent delivery device 329 after charging the valve 334 to select the enzyme-labeled reagent tank 331. The reagent and carrier are stirred sufficiently at the position $S_2$ by supplying the air stream from the small mouth portion 311b with the aid of the air pump 327 to effect a second antigen-antibody reaction.

During a third revolution of the turntable 312, at the position $S_{22}$, the U-shaped tube 311 and carrier are washed by means of the washing pump 324 and discharge pump 328 to perform a second B-F separation. Next, a given amount of the color reagent is delivered into the U-shaped tube 311 by the reagent delivery device 329 after changing the valve 334 to select the color reagent tank 332. Then, the color reagent and carrier are stirred by means of the air pump 327 to start a reaction of the color reagent with the labeling enzyme of the enzyme-labeled reagent bound with the carrier 321.

In a fourth revolution of the turntable 312, at the position $S_{19}$ a reaction liquid in the U-shaped tube 311 is sucked into the colorimeter 322 to effect the colorimetric measurement.

At the position $S_{20}$, the carrier 321 is sucked out of the U-shaped tube 311 via its large mouth portion 311a by the carrier discharge device 323. At the position $S_{22}$, the washing liquid is supplied into the U-shaped tube 311 via its large mouth portion 311a by means of the washing pump 324 and the wash liquid is sucked out of the tube by means of the discharge pump 328. The wash liquid remaining in the tube is discharged at the position $S_{23}$ by means of the discharge pump 328. In this manner, the U-shaped tube 311 is prepared for a next supply of a carrier. During the operations mentioned above, the nozzle 335 is transferred to the washing liquid tank 333 after the end of each reagent delivery operation so as to wash inner and outer walls of the nozzle 335 by means of the syringe 329.

The present invention is not limited to the embodiments explained above, but many modifications and alterations can be conceived, which are within the scope of the invention. In the above embodiments, the enzyme-labeled reagent is used to perform the enzyme-immuno-assay, but the radio-immuno-assay and flourescent-immuno-assay may be also adopted. Further, it is not always necessary to use a circular reaction line, but the reaction line can be formed by a snake chain. Moreover, in the embodiments using the carriers, the direct colorimetry may be effected, while the test liquid is caused to remain in the reaction vessel. In this case, if the carrier affects the measurement, it may be withdrawn from the reaction vessel prior to the colorimetry. Moreover, in all the above embodiments there is provided the single washing device, but a plurality of washing devices may be used. For instance, in the embodiment shown in FIG. 3, two washing devices may be arranged at diametrically opposite positions with the first washing and second B-F separating being performed by the first washing device and the first B-F separation and last washing being carried out by the second washing device. Even in such a case, the number of the washing devices can be decreased as compared with the case in which the four washing operations are carried out by four separate washing devices. Further, in the embodiments using the carriers, the reaction vessels may be discharged.

In the embodiments explained above, a single test item is measured by a single reaction line, but the multiple test items may be analyzed by a single reaction line. Further, in order to improve the reliability of analysis, the same test item may be measured by two reaction lines. Moreover, the deliveries of the reagents and buffer solution are carried out at different positions, but they may be effected at the same position. Then, the agitation may be performed only at a single position. Further, in the embodiment shown in FIG. 5, the delivery of the buffer solution prior to the carrier supply may be performed by the delivery device 25, and then the separate buffer solution delivery device 31 may be delected.

In the embodiments illustrated in FIGS. 21 and 24, the cuvette is washed after the cuvette supply, but prior to the sample delivery. However, since the cuvette is discharged from the turntable after analysis, saic preliminary washing may be dispensed with. Further, the test liquid may be colorimetered by introducing the test liquid from the cuvette into a flow cell of a separate colorimeter. Then, the delivery of the reaction stop liquid may be omitted. Further, in the embodiments, use is made of the cuvette of flat box shape, but cuvette may be formed in any desired shape. Moreover, in order to effect the reaction more stably, the cuvette may be immersed into a thermostat in the reaction line.

What is claimed is:

1. An automatic analysis method for detecting the presence of and analyzing biological substances in biological samples in an immunological manner, comprising:

(a) transporting a plurality of reaction vessels along an endless reaction line, said reaction vessels being provided with carriers onto with an antibody or anitgen has been fixed, said antibody or antigen for binding said biological substances;

(b) delivering said biological samples one per vessel into said reaction vessels;

(c) delivering labeled reagents containing labeling substances into the reaction vessels to initiate an antigen-antibody reaction with said biological samples;

(d) effecting a bound-free separation by separating biological substance bound by said antigen or antibody fixed with the carriers and free sample and labeled reagents by washing said reaction vessels and said carriers onto which said antibody or antigen had been fixed;

(e) measuring said biological substances in the samples by employing said labeling substances of the labeled reagents;

(f) discharging the carriers out of the reaction line; and (g) wherein during analysis of a specific one of said samples a reaction vessel transported along said endless reaction line is indexed to pass by a same washing position a plurality of times to effect at least a first washing and a second washing by means of a same washing device, at least one of said first washing and said second washing including said washing in step (d) to effect said bound-free separation.

2. A method according to claim 1, wherein the reaction line is a circular reaction line comprising a turntable, said reaction vessels being equidistantly spaced apart in a first circular array at uniform angular positions about a periphery of said turntable, said turntable being rotated intermittently at a given angular distance increment equal to the spacing between said reaction vessels.

3. A method according to claim 2, wherein step (a) includes suppling the carriers one per vessel into the reaction vessels one by one, and after steps (e) and (f) have been effected, step (g) includes washing the reaction vessels to prepare for a next analysis.

4. A method according to claim 3, wherein during a first revolution of the turntable after one of said carriers has been supplied into a reaction vessel in step (a), step (b) comprises delivering one of said samples into the reaction vessel and step (c) comprises delivering one of said labeled reagents into the reaction vessel to effect a first antigen-antibody reaction, said labeled reagents comprising an enzyme-labelled reagent; during a second revolution of the turntable, step (d) comprises washing the reaction vessel and the carrier therein to effect a first bound-free separation of biological sample bound by said antigen or antibody and free sample and labeled reagents and thereafter step (c) comprises again delivering one of said labeled reagents into the reaction vessel to start a second antigen-antibody reaction; during a third revolution of the turntable, step (d) comprises washing the reaction vessel and the carrier therein to effect a second bound-free separation of biological sample bound by said antigen or antibody and free sample and labeled reagents and step (e) comprises then delivering a color reagent including an enzyme substrate into the reaction vessel to form a test liquid; and during a fourth revolution of the turntable, step (e) comprises colorimetering the test liquid, step (f) comprises discharging the carrier from the reaction vessel and step (g) comprises washing the reaction vessel.

5. A method according to claim 4, wherein step (g) comprises washing the reaction vessel and carrier after supply of the carrier into the reaction vessel, but prior to the delivery of the sample into the reaction vessel.

6. A method according to claim 5, wherein prior to the supply of the carrier into the reaction vessel, a buffer solution is poured into the reaction vessel.

7. A method according to claim 4, wherein the supply and discharge of carrier, delivery of sample and reagent, and colorimetry are effected once every time the turntable is rotated by three said angular distance increments.

8. A method according to claim 7, wherein step (g) comprises carrying out a washing every time the turntable is rotated by one said angular distance increment.

9. A method according to claim 7, wherein the washing is effected at any one of three different washing positions every time the turntable is rotated by three distance increments by a washing device having said three said angular different washing positions.

10. A method according to claim 4, wherein on the turntable there are arranged second and third arrays of reaction vessels concentric with said first array and the supply and discharge of carrier, delivery of sample and reagents and measuring of said biological samples are effected for one reaction vessel every time the turntable is rotated by one said angular distance increment, while during both said second revolution and said third revolution, step (d) comprises simultaneously washing three reaction vessels respectively positioned in the first, second and third arrays.

11. A method according to claim 3, wherein during a first revolution of the turntable, step (a) includes supplying one of said carriers into a reaction vessel and then steps (b) and (c) comprise delivering sample and said labeled reagent into the reaction vessel to start an antigen-antibody reaction; during a second revolution of the turntable, step (d) comprises washing of the reaction vessel and the carrier therein to effect a bound-free separation and step (e) includes (i) delivering a color reagent for selectively reacting with said labeled reagent into the reaction vessel to form a test liquid; and during a third revolution of the turntable, step (e) comprises colorimetering the test liquid, performing step (f) and thereafter step (g) comprises washing the reaction vessel.

12. A method according to claim 11, wherein step (g) comprises washing the reaction vessel and carrier after supply of carrier, but prior to the delivery of sample and reagent.

13. A method according to claim 11, wherein step (a) comprises delivery of the carrier at a position on said reaction line disposed immediately after a position at which the discharge of carrier is performed in step (f), but prior to the washing position of step (g).

14. A method according to claim 1, wherein the reaction vessels are transported along the endless reaction line constituted by an endless belt which is intermittently rotated at a given distance increment in a vertical plane, said distance increment corresponding to a distance between adjacent reaction vessels disposed on said reaction line.

15. A method according to claim 1, wherein step (c) comprises delivering a plurality of liquids including said labeled reagent and buffer solution into the reaction vessels by means of a single delivery device.

16. A method according to claim 15, wherein step (c) comprises selectively delivering buffer solution, enzyme-labeled reagent and color reagent into the reaction vessels by said single delivery device.

17. A method according to claim 16, wherein the delivery device is washed every time a liquid different from a liquid which has been just delivered is to be delivered.

18. An automatic analysis method for detecting the presence of and analyzing biological substances in biological samples in an immunological manner, comprising:
(a) transporting a plurality of reaction vessels along an endless reaction line, said reaction vessels comprising cuvettes having an antibody or antigen fixed thereto, said antibody or antigen for binding said biological substances;
(b) delivering said biological samples one per vessel into said reaction vessels;
(c) delivering labeled reagents containing labeling substances into the reaction vessels to initiate an antigen-antibody reaction with said biological samples;
(d) effecting a bound-free separation by separating biological substance bound by said antigen or antibody fixed with the reaction vessels and free sample and labeled reagents by washing said reaction vessels and;
(e) measuring said biological substances in the samples by employing said labeling substances of the labeled reagents; and
(f) wherein during analysis of a specific one of said samples a reaction vessel transported along said endless reaction line is indexed to pass by a same washing position a plurality of times to effect at least a first washing and a second washing by means of a same washing device, at least one of said first washing and said second washing including said washing in step (d) to effect said bound-free separation, wherein the reaction line is a circular reaction line comprising a turntable, said reaction vessels being equidistantly spaced apart in a first circular array at uniform angular positions about a periphery of said turntable, said turntable being rotated intermittently at a given angular distance increment equal to the spacing between said reaction vessels, and wherein step (a) includes successively supplying the reaction vessels in the form of cuvettes having the antibody or antigen fixed thereto to cuvette holders provided along said periphery of the turntable, and after the measuring of said biological samples in step (e), the cuvette is discharged from the turntable.

19. A method according to claim 18, wherein during a first revolution of the turntable after the supply of a cuvette into the turntable, step (b) includes delivering a sample into the cuvette and step (c) comprises delivering one of said labeled reagents into the cuvette to effect a first antigen-antibody reaction; during a second revolution of the turntable, step (d) comprises washing the cuvette to effect a first bound-free separation and step (c) comprises then delivering one of said labeled reagents into the cuvette to start a second antigen-antibody reaction; and during a third revolution of the turntable, step (d) comprises washing the cuvette to effect a second bound-free separation and step (e) comprises delivering a color reagent including an enzyme substrate into the cuvette to form a test liquid; and during a fourth revolution of the turntable; step (e) comprises colorimetering the test liquid and step (f) comprises discharging the cuvette from the turntable.

20. A method according to claim 19, wherein step (f) comprises washing the cuvette after supply of the cuvette into the turntable, but prior to the delivery of the sample into the cuvette.

21. A method according to claim 19, wherein the supply and discharge of cuvette, delivery of sample and reagent, and measuring of said biological samples are effected once every time the turntable is rotated by three said angular distance increments.

22. A method according to claim 21, wherein step (f) comprises carrying out a washing every time the turntable is rotated by one of said angular distance increments.

23. A method according to claim 21, wherein step (f) comprises carrying out a washing every time the turntable is rotated by three of said angular distance increments by a washing device having three different washing positions.

24. A method according to claim 18, wherein during a first revolution of the turntable, step (a) comprises supplying a cuvette onto the turntable and steps (b) and (c) respectively comprise delivering sample and said labeled reagent into the cuvette to initiate an antigen-antibody reaction; during a second revolution of the turntable, step (d) comprises washing the cuvette to effect a bound-free separation and step (e) includes delivering a color reagent for selectively reacting with said labeled reagent into the cuvette to form a test liquid; and during a third revolution of the turntable, step (e) comprises colorimetering the test liquid and step (f) comprises discharging the cuvette from the turntable.

25. A method according to claim 24, wherein step (f) comprises washing the cuvette after supply of the cuvette, but prior to the delivery of sample and reagent.

26. A method according to claim 24, wherein step (a) comprises delivery of the cuvette at a position on said reaction line disposed immediately after the position at which the discharge of cuvette is performed in step (f) but prior to the washing position of step (f).

27. An automatic analysis method for detecting the presence of and analyzing biological substances in biological samples in an immunological manner, comprising:

(a) transporting a plurality of reaction vessels along an endless reaction line, said reaction vessels being provided with an antibody or antigen fixed onto at least a part of the inner walls of said reaction vessels, said antibody or antigen for binding said biological substances;

(b) delivering said biological samples one per vessel into said reaction vessels;

(c) delivering labeled reagents containing labeling substances into the reaction vessels to initiate an antigen-antibody reaction with said biological samples;

(d) effecting a bound-free separation by separating biological substance bound by said antigen or antibody fixed with said inner walls of the reaction vessels and free sample and labeled reagents by washing said reaction vessels and said antibody or antigen fixed onto at least a part of the inner walls of the reaction vessels;

(e) measuring said biological substances in the samples by employing said labeling substances of the labeled reagent;

(f) discharging the reaction vessels out of the reaction line; and (g) wherein during analysis of a specific one of said samples a reaction vessel transported along said endless reaction line is indexed to pass by a same washing position a plurality of times to effect at least a first washing and a second washing by means of a same washing device, at least one of said first washing and said second washing including said washing in step (d) to effect said bound-free separation.

* * * * *